United States Patent [19]
Poirier

[11] Patent Number: 6,022,683
[45] Date of Patent: Feb. 8, 2000

[54] METHODS FOR ASSESSING THE PROGNOSIS OF A PATIENT WITH A NEURODEGENERATIVE DISEASE

[75] Inventor: Judes Poirier, Boisbriand, Canada

[73] Assignee: Nova Molecular Inc., Montreal, Canada

[21] Appl. No.: 08/766,975

[22] Filed: Dec. 16, 1996

[51] Int. Cl.$^7$ .................................................. C12Q 1/00
[52] U.S. Cl. ................................................................ 435/4
[58] Field of Search ................................. 435/4, 6, 91.2, 435/91.21

[56] References Cited

U.S. PATENT DOCUMENTS

| 5,508,167 | 4/1996 | Roses et al. | ............................... 435/6 |

FOREIGN PATENT DOCUMENTS

| 2716894-A1 | 9/1995 | France . | |
| 94/09155 | 4/1994 | WIPO . | |
| 95/16791 | 6/1995 | WIPO . | |
| 29257 | 11/1995 | WIPO | ........................ 435/6 |
| WO 96 02670A | 2/1996 | WIPO . | |
| WO 96 03656A | 2/1996 | WIPO . | |

OTHER PUBLICATIONS

Farlow et al., 1996, "Apolipoprotein E Genotype and Gender Influence Response to Tacrine Therapy", Ann. N.Y. Acad. Sci. 802:101–110.

Timchenko et al., 1996, "Trinucleotide repeat disorders in humans: discussions of mechanisms and medical issues", FASEB J. 10:1589–1597.

Salvatore et al., 1995, "Apolipoprotein E in sporadic and familial Creutzfeldt–Jakob disease" Neurosci. Letters 199:95–98.

Brouillet et al., 1995, "Chronic mitochondrial energy impairment produces selective striatal degeneration and abnormal choreiform movements in primates", Proc. Natl. Acad. Sci. USA 92:7105–7109.

Hardy et al., Alzheimer's Disease Collaborative Group, "Apolipoprotein Genotype E and Alzheimer's Disease", Lancet 342:737–738, 1993.

Bartus et al., "The Cholinergic Hypothesis of Geriatric Memory Dysfunction", Science 217:408–417.

Bertrand et al., "Association of Apolipoprotein E Genotype with Brain Levels of Apolipoprotein E and Apolipoprotein J(clusterin) in Alzheimer's, Disease", Mol. Brain Res. 33:174–178, 1995.

Boyle et al., "Apolipoprotein E Associated with Astrocytic Glia of the Central Nervous System and With Non Myelinating Glia of the Peripheral Nervous System", J. Clin. Invest. 76:1501–1513, 1985.

Corder et al., "Gene Dose of Apolipoprotein E Type 4 Allele and the Risk of Alzheimer's Disease in Late Onset Families", Science 261:921–923, 1993.

Goodrum, "Cholesterol Synthesis is Down–Regulated During Regeneration of Peripheral Nerve", J. Neurochem 54:1709–1715, 1990.

Koo et al., "Obligatory Role of Cholesterol and Apolipoprotein E in the Formation of Large Cholesterol–Enriched and Receptor Active High Density Lipoproteins", J. Biol. Chem 260:11934–11943, 1985.

Leblanc et al., "Regulation of Apolipoprotein E Gene Expression After Injury of the Rat Sciatic Nerve", J. Neurosis. Res. 25:162–171, 1990.

Masliah et al., "Neurodegeneration in the Central Nervous System of apoE–Deficient Mice", Exp. Neurol. 136:107–122, 1995.

Masliah et al., "Apolipoprotein E Role In Maintaining the Integrity of the Aging Central Nervous System in: Apolipoprotein E and Alzheimer's Disease", Springer–Verlag, Heidelberg pp. 59–73, 1996.

Nalbantoglu et al., "Predictive Value of Apolipoprotein E Genotyping in Alzheimer's Disease . . . ", Ann. Neurol. 36:889–895, 1994.

Noguchi et al., "Apolipoprotein E and Alzheimer's Disease", Lancet (letter) 342:737, 1993.

Payami et al., "Apolipoprotein E and Alzheimer's Disease", Lancet (letter) 342:738, 1993.

Poirier et al., "Apolipoprotein E Allele As a Predictor of Cholinergic Deficits and Treatment Outcome in Alzheimer's Disease", Proc. Natl. Acad. Act. 92:12260–12264, 1995.

Poirier et al., "Cholesterol Synthesis and Lipoprotein Reuptake During Synaptic Remodelling in Hippocampus in Adult Rats", Neuroscience 55:81–90, 1993.

Poirier et al., "Apolipoprotein E Polymorphism and Alzheimer's Disease", Lancet 342:697–699, 1993.

Poirier et al., "Apolipoprotein E, Cholinergic Integrity and Synaptic Plasticity in Alzheimer's Disease in: Apolipoprotein E and Alzheimer's Disease", Springer–Verlag, Heidelberg pp. 22–32, 1996.

Poirier et al., "Astrocytic Apolipoprotein E mRNA and GFAP mRNA in Hippocampus After Entorhinal Cortex Lesioning", Mol. Brain Res. 11:97–106, 1991.

Poirier et al., "Cloning of Hippocampal poly(A) RNA Sequences that Increase After Emtorhinal Cortex Lesion in Adult Rat", Mol. Brain Res. 9:191–195, 191.

Reed et al., "Lower Cognitive Performance in Normal Older Adult Male Twins Carrying the Apolipoprotein E Epsilon 4 Allele", Arch Neurol. 51:1189–1192, 1994.

Rothe et al., "Uptake of Endoneurial Lipoprotein Into Schwann Cells and Sensory Neurons is Mediated by Low Density Lipoprotein Receptors and Stimulated After Axonal Injury", J. Neurochem. 57:2016–2025, 1991.

Schellenberg et al., "Genetic Analysis of Familial Alzheimer's Disease", Neurobiol. Aging 17:149, 1996.

*Primary Examiner*—Laurie Scheiner
*Assistant Examiner*—J. S. Parkin
*Attorney, Agent, or Firm*—Kristina Bieker-Brady; Clark & Elbing LLP

[57] ABSTRACT

The present invention provides a method for the determining the appropriate therapy and/or prognosis for a patient diagnosed with a non-Alzheimer's disease (AD) neurological disease based upon the patient's apoE allele load. The invention also provides a method for the identification of human subjects with a non-AD neurological disease that are likely to respond in clinical trials that test pharmaceuticals useful in the treatment of neurological diseases.

14 Claims, 14 Drawing Sheets

METHODS FOR ASSESSING THE PROGNOSIS OF A PATIENT WITH A NEURODEGENERATIVE DISEASE

BACKGROUND OF THE INVENTION (a) Field of the Invention

The invention relates to the treatment of neurological disease.

(b) Description of Art

Apolipoprotein E (apoE) functions as a ligand in the process of receptor mediated internalization of lipid-rich lipoproteins. ApoE is probably also involved in reverse lipid transport. In the central nervous system (CNS), apoE plays a central role in the mobilization and redistribution of cholesterol and phospholipid during membrane remodeling associated with synaptic plasticity (Poirier, J. et al., 1991, Mol. Brain. Res., 9:191–195; Poirier, J. et al., 1991, Mol. Brain. Res., 11:97–106; Poirier, J. et al., 1993, Neuroscience, 55:81–90). The importance of apoE in the brain is further underscored by the absence of other key plasma apolipoproteins such as apoA1 and apoB in the brain (Roheim, P. S. et al., 1979, Proc. Natl. Acad. Sci., 76:4646–4649).

The apoE gene on chromosome 19 has three common alleles (E2, E3, E4), which encode three major apoE isoforms. The frequency of the apoE4 allele has been shown to be markedly increased in sporadic Alzheimer's Disease (AD) (Poirier, J. et al., 1993, Apolipoprotein E phenotype and Alzheimer's Disease, Lancet, 342:697–699; Noguchi, S. et al., 1993, Lancet (letter), 342:737) and late onset familial Alzheimer's disease (AD) (Corder, E. H. et al., 1993, Science, 261:921–923; Payami, H. et al., 1993, Lancet (letter), 342:738). This gene dosage effect was observed in both sporadic and familial cases (i.e., as age of onset increases, E4 allele copy number decreases). Women, who are generally at a greater risk of developing Alzheimer's disease, show increased E4 allele frequency when compared to age matched men.

The cholinergic hypothesis of geriatric memory dysfunction raised some fundamental questions regarding the heterogeneity of responses toward different cholinomimetics in AD (Bartus, R. T. et al., 1982, Science, 217:408–417). The absence of clear beneficial effects of choline and lecithin on geriatric patients with and without AD is still perplexing. Furthermore, multiple clinical studies using esterases inhibitors such as physostigmine and tacrine have shown that contrary to young subjects, the optimal acute dose necessary to facilitate performance on memory tasks varied considerably among individual aged subjects (Bartus, R. T. et al., 1982, Science, 217:408–417).

Neurological diseases provide a unique series of complications for the clinicians, patients, and care givers; the diseases often progress rapidly and disrupt a vast number of major life functions. The progressive nature of these diseases makes the passage of time a crucial issue in the treatment process. Treatment choices in the neurological disease context are complicated by the fact that it often takes a significant period of treatment to determine whether or not a drug is having a therapeutic effect. Accordingly, treatment with the most effective drug or drugs is often delayed while the disease continues to progress. A method which would allow one to predict which patients will respond to specific therapeutics and dosages would provide physical and psychological benefits. As healthcare becomes increasingly inaccessible, the ability to allocate healthcare resources effectively also becomes increasingly important.

SUMMARY OF THE INVENTION

I have discovered a method for predicting the prognosis for patients having a neurological system disease. Specifically, I have found a method for determining responsiveness to cholinomimetic drug therapies, the relative age of onset, and the relative rate of progression of various diseases. From these discoveries I have developed an approach, referred to herein as pharmacogenetics, for profiling patients already diagnosed with a neurological disease. Pharmacogenetics provides a prognosis for the patient, including determination of the most effective drug (where appropriate) and drug dosage (if any). My method allows clinicians, patients, and family members to make informed choices about therapeutic regimes. Furthermore, where more than one therapeutic exists, the pharmacogenetic methods of the invention allow the clinician to avoid serially administering therapeutics until a therapeutic which works is discovered through trial and error; with pharmacogenetics an appropriate therapeutic can be administered on the first round of therapy. This method will provide more rapid treatment with the appropriate drug and drug dose. Even where drug therapy is inappropriate, the method will provide patients with a prognosis and will allow the patient the option of avoiding what may be needless drug side-effects.

The pharmacogenetic method has an additional advantage when utilized in the field of drug testing. The method allows the patient being considered for enrollment in a drug trial to be classified as likely or unlikely to benefit from a cholinomimetic therapy. If the patient is likely to respond to a cholinomimetic, and the drug being tested is not a cholinomimetic, then the patient may be physically unsuitable for the trial or it may be ethically inappropriate. Conversely, patients likely to respond to cholinomimetics will provide more statistically useful data on novel cholinomimetic therapeutics. Patients unlikely to respond to cholinomimetic drugs are particularly good candidates for non-cholinomimetic therapies from both a physical and ethical perspective.

In the first two aspects, the invention provides a method of creating a prognosis protocol for a patient diagnosed with a neurological disease or Alzheimer's disease (AD). The method includes: a) identifying a patient already diagnosed with said disease; b) determining the apoE allele load of said patient; and c) converting the data obtained from step b into a prognosis protocol. The prognosis protocol may include a prediction of drug efficacy, a prediction of patient outcome, or both. In preferred embodiments of these aspects, the methods may further include the steps of obtaining a patient profile, which may, preferably, include the patient's sex and/or genotype (e.g., presenilin genotype or apolipoprotein E genotype).

In other preferred embodiments of the neurological disease method, the patient is a patient diagnosed with a disease selected from the group consisting of: a) prion disease, a pathology of the developing nervous system, a pathology of the aging nervous system, nervous system injury, a coma, an infection of the nervous system, a dietary deficiency, and cardiovascular injury. For example, the patient may have been diagnosed with Creutzfeldt-Jakob disease; a congenital defect in amino acid metabolism (e.g., arginosuccinic aciduria, cystathionuria, histidinaemia, homocystinuria, hyperammonaemia, phenylketonuria, and tyrosinaemia); fragile X syndrome; neurofibromatosis; Huntington's disease; depression; amyotrophic lateral sclerosis; multiple sclerosis; stroke; Parkinson's disease; or multiple infarcts dementia.

In a third and fourth aspects, the invention provides a method for identifying non-AD patients for participation in clinical trail of a drug for the treatment of a non-AD neurological disease or AD. The methods include: a) identifying a patient already diagnosed with said non-AD neurological disease or AD; b) determining the apoE allele load of said patient; and c) converting the data obtained from step b into a prognosis protocol. The prognosis protocol provides an indication of whether or not said patient is a candidate for a cholinomimetic drug trial or non-cholinomimetic drug trial. Patients who have one or more apoE4 alleles are poor candidates for the trial of a cholinomimetic drug trials.

In a fifth aspect, the invention provides a method for determining whether a human will respond to cholinomimetic cognitive enhancer. The method includes: a) obtaining a patient profile on said human; b) determining the apoE allele load of said human; and c) selecting those humans having at least one apoE2 or apoE3 allele as recipients of said cholinomimetic drug. In preferred embodiments, the patients selected to receive said enhancer have no apoE4 alleles.

In a related aspect, the invention provides a kit for performing pharmacogenetic analysis. The kit includes a means for converting the patient profile into a prognosis protocol. In a preferred embodiment, the kit contains a means for performing the steps of the conversion. In another preferred embodiment, the kit contains a means for compiling the data for said patient profile and for formatting said patient profile.

Therapeutic agents relevant to the present invention include both cholinomimetic and non-cholinomimetic drugs used for the treatment of neurological disease. Cholinomimetic drugs may be selected from the group consisting of inhibitors of acetylcholine degradation, inducers of acetylcholine synthesis, acetylcholine agonists or mimics, and muscarinic M2-receptor antagonists. It should be noted that the therapies suggested by the pharmacogenetic method may be used alone, or in combination with other known therapies that are not otherwise contraindicated for the patient.

For the purpose of the present invention the following terms are defined below.

"Cognitive enhancers" means drugs which enhance a) memory performance, whether it is verbal memory, spatial memory, or factual memory and b) learning capacity.

"Cholinomimetic therapies" means drugs that mimic the function of acetylcholine or enhance the activity of remaining acetylcholine synthesizing cells. These drugs include, but are not limited to, inhibitors of acetylcholine degradation (acetylcholine esterase inhibitors like tacrine), drugs that mimic acetylcholine structure and function (agonist: muscarinic M1-receptor agonist is a typical example), drugs that block acetylcholine uptake by neurons and drugs that interact pre-synaptic receptors to induce acetylcholine release from cholinergic neurons.

"ApoE probes" means nucleic acid probes or ApoE allele specific antibodies that selectively recognize the apoE2, apoE3 or apoE4 alleles or proteins, respectively.

"Non-AD Neurological disease" means any disease other than Alzheimer's disease, which involves the neuronal cells of the nervous system. Specifically included in preferred embodiments are: prion diseases (e.g., Creutzfeldt-Jakob disease); pathologies of the developing brain (e.g., congenital defects in amino acid metabolism, such as arginosuccinic aciduria, cystathionuria, histidinaemia, homocystinuria, hyperammonaemia, phenylketonuria, and tyrosinaemia, and fragile X syndrome); pathologies of the mature brain (e.g., neurofibromatosis, Huntington's disease, depression, amyotrophic lateral sclerosis, multiple sclerosis, and stroke); conditions that affect the elderly (e.g. Parkinson's disease, multiple infarcts dementia, and stroke); and multitude of other ills that can affect the brain (e.g., brain mishaps, brain injury, coma, infections by various agents, dietary deficiencies, and cardiovascular accidents). In preferred embodiments, the invention includes stroke and AD. In the most preferred embodiments, the invention includes AD.

"Alzheimer's Disease (AD)" means a pathology characterized by an early and extensive loss of entorhinal cortex neurons. AD patients may be identified by progressive and degenerative effects on the brain which cannot be attributed to causes other than AD.

"Already diagnosed" means already diagnosed as having the neurological disease, having a genetic predisposition to the disease, or both.

"Patient profile" means data pertaining to the patient for whom the pharmacogenetic analysis is being performed. Data may include information on the patient's diagnosis, age, and genotype. The patient's profile may also include materials from the patient such as blood or purified DNA.

"ApoE genotyping" means determination of the type and number of apoE alleles present n the patient, whether by nucleic acid sequencing or examination of apoE protein present in the patient.

"Allele load" means the relative ratio of apoE2, 3, and 4 alleles in the patient's chromosomal DNA. The allele load may be determined by comparing the relative numbers of the patient's already known apoE allele types.

"Prognosis protocol" means a therapy plan provided to the clinician or patient using the pharmacogenetic method. The prognosis protocol includes an indication of whether or not the patient is likely to respond positively to a cholinomimetic therapeutic. In preferred embodiments, the protocol also includes an indication of the drug dose to which the patient is most likely to respond.

"The pharmacogenetic method" is a method whereby genetic and diagnostic data, including the patient's neurological diagnosis and the patient's apoE genotype are processed to provide therapeutic options and prognoses.

DETAILED DESCRIPTION OF THE INVENTION

Figure 1:
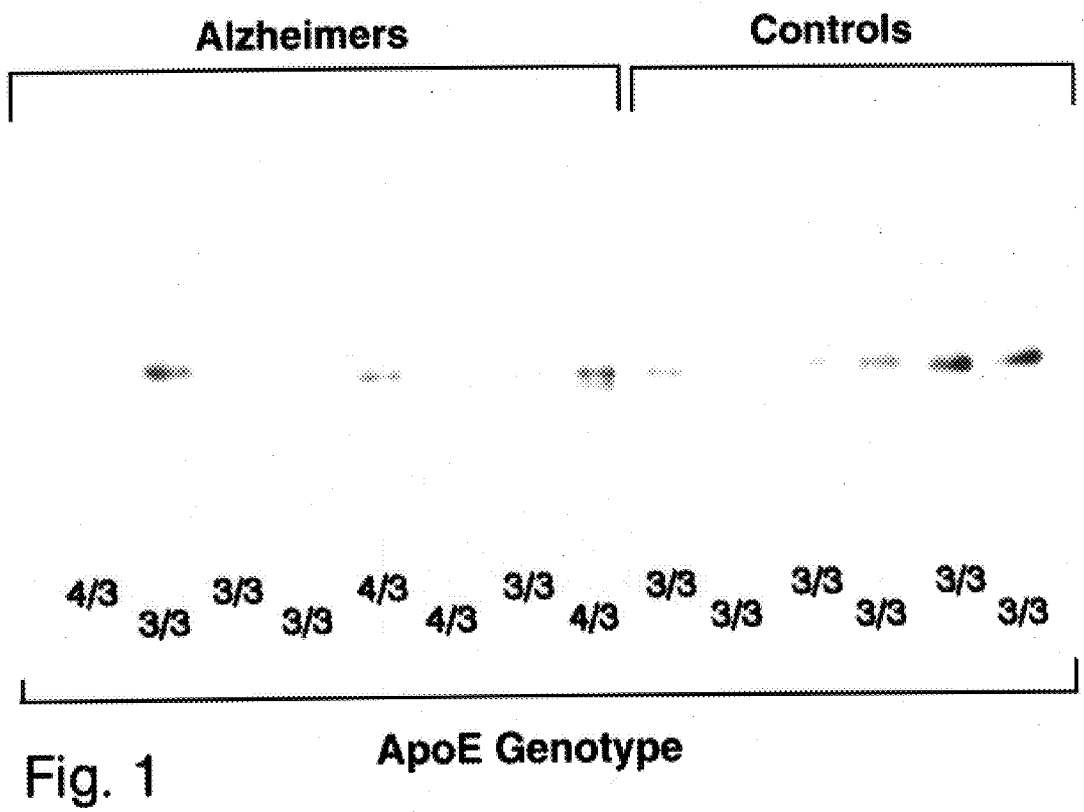
FIG. 1 is a Western blot analysis of apoE protein levels in the hippocampus of AD and non-AD individuals.

Here we show that correlation of age, sex, genotype, and apoE allele load may be used to determine the appropriate drug or drugs, dosage, and prognosis for a given AD or non-AD patient. The prognosis can include a prediction of both relative age of onset and rate of progression.

Losses of cholinergic neurons and/or ChAT activity are well known hallmarks of AD (Perry, E. K. et al., 1977, J. Neurol. Sci., 34:247–265; Davies, P. et al., 1976, Lancet, 2:1403). I investigated the relationship between the apoE4 genotype and cholinergic deficits, and I observed that the greater the number of apoE4 allele the lower the apoE levels. Furthermore, reduction in ChAT activity in the hippocampus and temporal cortex of AD cases is inversely proportional to the apoE4 allele copy number (i.e. where the apoE4 allele copy number is increased the ChAT activity is decreased). In addition, I found that another presynaptic marker of cholinergic projection, the nicotinic receptor, was markedly reduced in apoE4 AD subjects. Conversely, I found that the typical post-synaptic marker, M1-muscarinic receptor, unaltered in AD versus non-AD subjects, whether apoE4 is present or not. The M2-muscarinic receptor, a composite pre- and post-synaptic marker, is also unaffected by the apoE4 allele gene dosage. I have also found that the presence of the apoE4 allele lowers the age of onset of neurological disease and worsens the prognosis.

The above findings clearly indicate the existence of distinct genetic entities in neurological disease which correlate with differential degrees of alterations of cholinergic innervation. In turn, the innervation level correlates with the prognosis, including the ability to respond to cholinomimetic drugs.

I believe the correlation between apoE4 allele load and reductions in ChAT activity and nicotinic receptors may be explained by at least two distinct phenomena. First, phospholipids such PC and PE, that can serve precursors to choline in the synthesis of Ach, could be transported into neurons via the classical apoE-LDL receptor pathway. An isoform-dependent impaired regulation of the transport of phospholipids in the brain of apoE4 carriers could explain the reduced levels of PC, PE and choline reported in AD (Pettegrew, J. W., 1989, Ann. NY Acad. Sci., 568:5–28; Nitch, R. M. et al., 1992, Proc. Natl. Acad. Sci., 89:1671–1675). This, in turn, may lead to decreased Ach synthetic capacities. This hypothesis is consistent with membrane defects reported in AD subjects such as changes in membrane fluidity in the hippocampus and in the platelets of AD patients. The loss of cholesterol reported in AD and the effect of apoE4 on nicotinic binding activity are consistent with the apoE4/impaired lipid homeostasis hypothesis.

In addition to the above, the reduction in neuronal ChAT activities and choline levels in both AD and non-AD patients could parallel the loss of cholinergic neurons. The analysis of the number of acetylcholinesterase-positive neurons in the nucleus basalis of Meynert (NBM) and the diagonal band of Broca (DBB) in AD patients revealed marked losses of cholinergic neurons in apoE4 carriers versus apoE3 homozygous AD cases.

Although initially made in AD patients, I believe my observation regarding apoE allele load and drug therapies can be generalized to non-AD neurological diseases because the underlying mechanism altered by the apoE allele load is not AD-specific. My discovery indicates that the apoE4 allele load, taken together with the patient profile parameters, can predict individual variations in brain cholinergic systems. Prospective-retrospective analyses of patients which are either good or poor responders to cholinomimetics is presented in the Examples.

Cholinomimetic drugs are known to enhance cognitive performance in both young and old subjects carrying at least one apoE2 or apoE3 allele. In apoE2 and apoE3 individuals cognitive performance could be restored or enhanced by the administration of cholinomimetics such as acetylcholine agonists (e.g. the M1-agonist xanomeline, available from Eli Lilly), M2 receptors-antagonist (e.g., BIBN-99 from Boehringer Ingeilheim), inhibitors of acetylcholine degradation (e.g., tacrine, available as Cognex™ from Parke-Davis, or E-2020, available from Pfizer) in subjects carrying apoE2 or apoE3 but not apoE4. Pharmacogenetics allows the physician to select the most appropriate treatment from the several available, for a given patient.

The present invention will be more readily understood by referring to the following examples which are given to illustrate the invention rather than to limit its scope.

EXAMPLE I

Determination of apoE Levels and Allele Load

Figure 2:
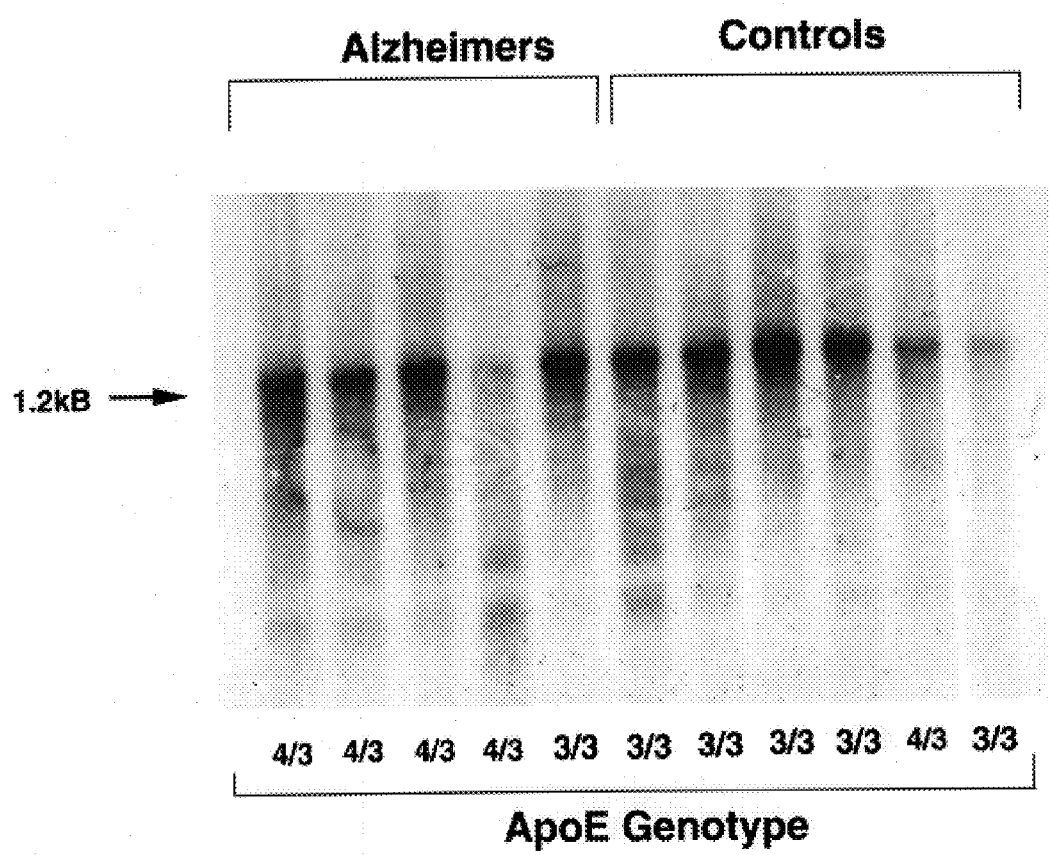
FIG. 2 is a Northern blot analysis of the apoE mRNA expression in the hippocampus of AD and non-AD individuals.
Figure 3A:
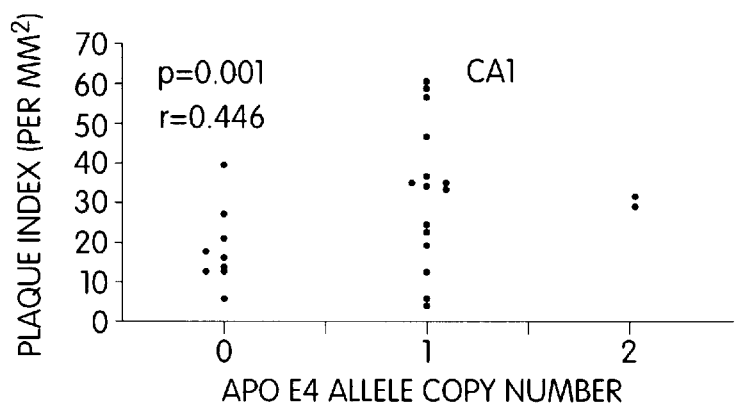
FIGS. 3A–3F are graphs illustrating E4 allele copy number, tangles and senile plaque densities in the hippocampus in AD.
Figure 3B:
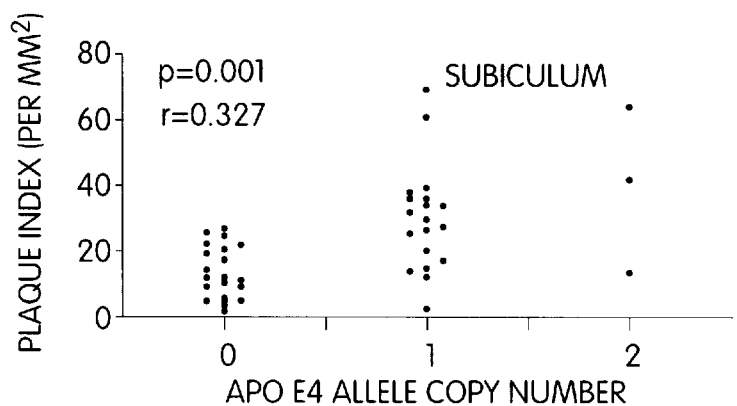
Figure 3C:
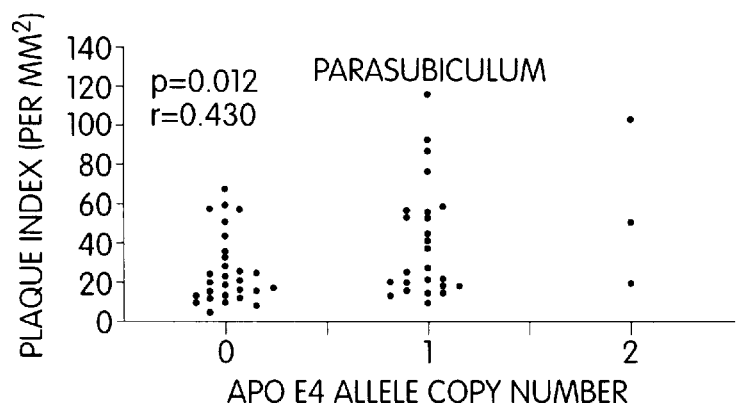
Figure 3D:
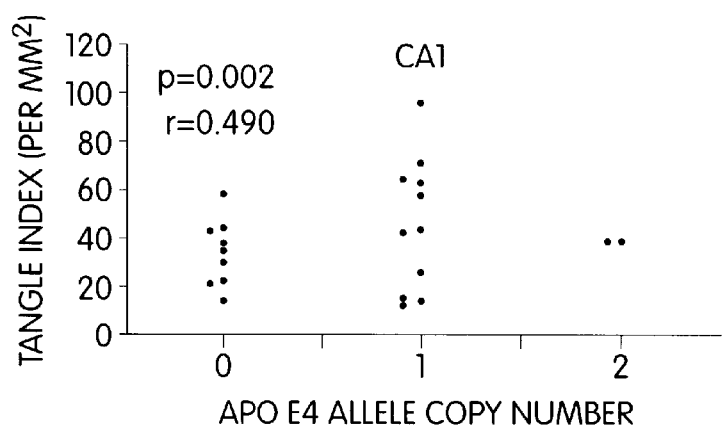
Figure 3E:
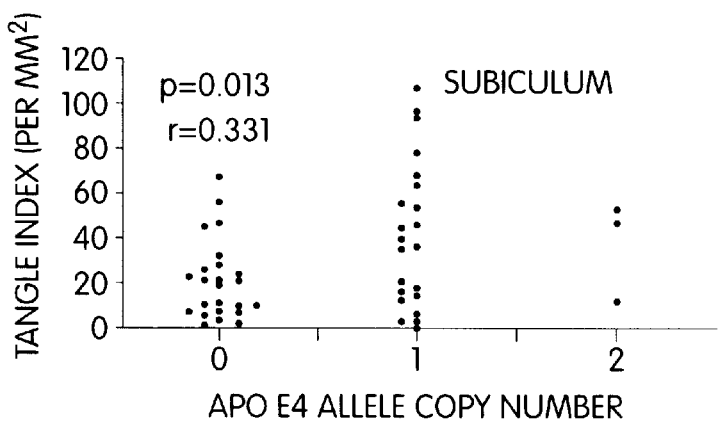
Figure 3F:
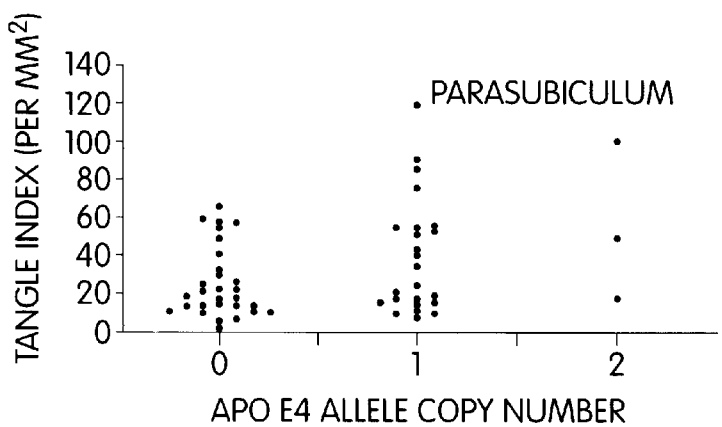

FIGS. 1 and 2 illustrate Western and Northern blot analyzes of apoE levels in the hippocampus of non-AD and AD patients as a function of their respective genotype.

Frozen hippocampi from post-mortem patients were obtained from the Douglas Hospital Brain Bank in Montréal. Age and sex were matched and post-mortem delays were similar from the two groups (~14 hrs). Post-mortem delays up until 24 hours have little impact on apoE stability (Lehtimaki, T., 1991, Clin. Chim. Acta, 203:177–182) and it can be stored at −80° C. for several months without noticeable trace of degradation. Hippocampal total RNA was extracted and quantified by oligo(dT) hybridization as described previously (Poirier, J. et al., 1991, Mol. Brain. Res., 11:97–106). Hybridization protocol of the full length apoE cRNA probe used in these experiment was described before (Poirier, J. et al., 1991, Mol. Brain. Res., 9:191–195). High molecular weight DNA was isolated from frozen cerebellum or temporal cortex as adapted from Goelz et al. (Goelz, S. E. et al., 1986, Biochem. Biophys. Res. Comm., 130:118–126).

ApoE genotype was determined by allele-specific extension of purified brain DNA using a modification of the method of Main et al. (Main, R. F. et al., 1991, J. Lipid. Res., 32:183–187). The primers labeled D, E, F, G, and H were synthesized for us by Genosys Biotech (The Woodland, TX); the primer sequences are given in Main et al. (Main, R. F. et al., 1991, J. Lipid. Res., 32:183–187). Reactions were carried out in a volume of 50 uL containing 1 ug of DNA; deoxyadenosine triphosphate, deoxycytidine triphosphate, deoxythymidine triphosphate and deoxy guanosine triphosphate, each 0.2 mmol/L; 10% dimethyl sulfoxide; 12.5 pmol of either primer D, E, F, G; 25 pmol of primer H; and 10 uL of 10 PCR reaction buffer (Vector Biosystem, Toronto, ONT.). The DNA in the reaction mixture was first denatured for 10 min. at 96° C. and then cooled to 4° C. One unit of Taq polymerase (Vector Biosystem, Toronto, ONT.) was then added to each sample. Each sample was reheated for 2 min. at 96° C. and subjected to 30 cycles in a thermal cycler with each cycle consisting of a 10 sec denaturation at 96° C., 30 sec annealing at 58° C. and 1 min. extension at 65° C. The reaction products were visualized by electrophoresis of 10 uL of the reaction mixture in a 1% agarose gel containing TPE buffer (0.08 mol/L Tris-phosphate, 0.002 mol/L EDTA) and ethidium bromide (0.15 ug/mL) for 1 hr at 67 v. The gels were then photographed and the banding profile was compared to known standards.

Briefly, 50 ug of hippocampal homogenate, pre-treated with 1 u of neuraminidase, were loaded on a 25 cm long SDS polyacrylamide gel (10%) and run for 3 hours at room temperature. Proteins were transferred on nitrocellulose filter in the BIORAD™ Trans-blot cell and detection of the apoE band was done with a poly clonal antibody raised against human apoE (International Immunology Corp., CA, Dil. 1:2000). Adsorption of the antibody with purified apoE completely blocked the detection of the human apoE band at MW 34–36 kDa. Molecular weight markers (Rainbow markers, Amersham) were run in adjacent wells while visualization of the bands was done with a chemiluminescence detection kit (Amersham, Cat. No. RPN 2100). Quantification of the autoradiographic signals was done on the MCID image analysis system (Ste-Catherine, Ontario) equipped with the 1D-gel analysis software.

Results

Figure 10:
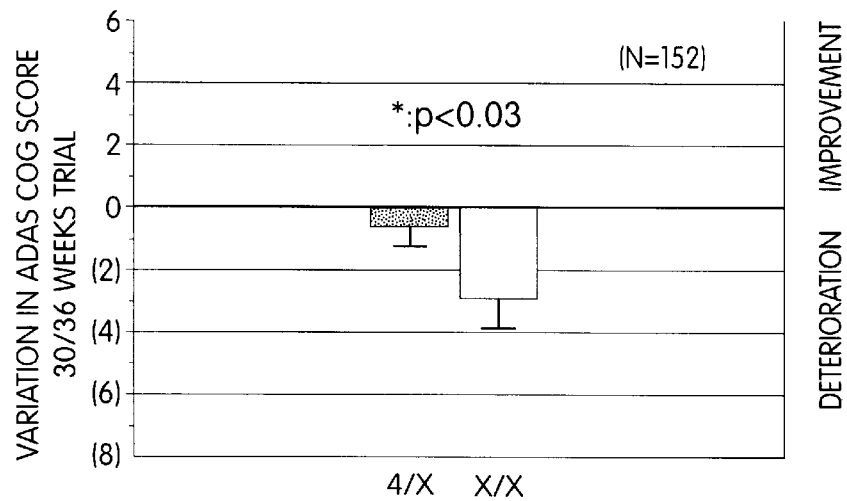
FIG. 10 is a graph of the effect of the presence of the apoE4 allele on the ADAS-COG Scores in FIGS. 9A and 9B.
Figure 11:
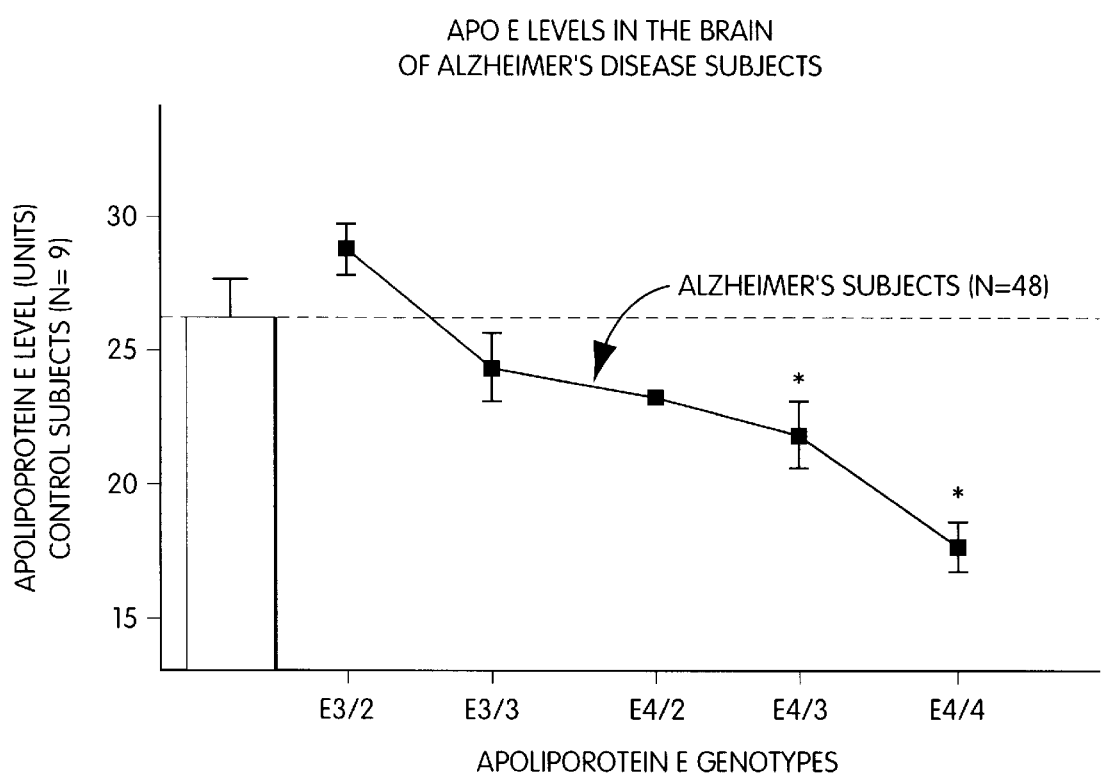
FIG. 11 is a graph of the brain apoE levels in AD subjects as a function of the apoE allele load.

In the AD brain, apoE mRNA was shown to be present but not up-regulated in response to cell loss and deafferentation. I have proposed that the synaptic loss reported in apoE4/AD subjects could be the result of a selective impairment of the apo E/LDL receptor pathway. FIG. 10 illustrates levels of apoE measured in the brain of AD subjects with different genotypes as well as in control subjects with apoE3/2 and apoE3/3 genotypes. Of the ~90 neuropathological elderly control subjects that I have examined so far (using standard criteria), none of those fitting the AD criteria were found to carry the E4 allele. A significant reduction in apoE tissue concentration was measured in apoE4 carriers versus non-E4 subjects. Interestingly, the risk of developing AD, the accumulation of senile plaques and tangles in the AD brain and the loss of cholinergic function in AD follow a genotype gradient: increase in damage from E2/2→E3/3→E4/4, the latter genotype representing the worse case scenario.

I believe that the most important observation from this data is the fact that the AD pathology is much more severe (cell loss, deafferentation and increased GFAP expression, etc.) in apoE4 AD carriers than it is in the apoE4-negative AD subjects. Yet, apoE levels, which should be increased in response to damage and cell loss, are in fact decreased in those same apoE4 individuals.

Pathophysiological consequences of having low apoE levels if you are a life long apoE4/AD carrier: In order to address the consequences of being an apoE A4 carrier, I have examined apoE/apoB (LDL) receptor expression (cholesterol internalization) and HMG-CoA reductase expression (cholesterol synthesis) in the hippocampus AD and control subjects with different apoE genotypes to assess the consequences of the poor delivery of lipids in E4 carriers. Table 1 summarizes the mRNA prevalences measured for the LDL receptor, HMG-CoA reductase and glial fibrillary acidic protein (GFAP) in post-mortem brains of control and AD subjects with known apoE genotypes. Betatubulin was used as a non-changer transcript to adjust for RNA loading in the gels. GFAP mRNA prevalence, a well known marker of local tissue damage is markedly increased in apoE4 carriers when compared to apoE3/3 AD subjects: supporting the notion of more severe damages in the brain of apoE4 carriers. The LDL receptor and HMG-CoA reductase mRNA prevalence were found to be increased in AD subjects carrying the apoE4 allele when compared to non-E4 carriers. This double induction of cholesterol internalization and synthesis is consistent with results obtained in fibroblasts and macrophages cultured in absence of cholesterol in which, both cholesterol uptake (via the LDL receptor) and synthesis (via the HMG-CoA reductase) are markedly up-regulated to facilitate raises in intracellular cholesterol.

TABLE 1 mRNA Prevalence in the Hippocampus of AD

| | % OF CONTROLS | | |
|---|---|---|---|
| Genes | Apo E3/3 | Apo E4/3 | Apo E4/4 |
| GFAP | 110 | 365* | 345* |
| LDL | 86.5 | 173* | 170* |
| HMG-CoA | 87 | 191* | 152 |
| | N = 6 | N = 7 | N = 3 |

*: p < 0.05

In other words, the reduction of brain apoE in apoE4 carriers (the only lipoprotein carrier of the CNS) although moderate in size, is sufficient enough to shift cholesterol metabolism from its normal steady state of concentration to a depleted state. This forces cells to compensate by up-regulating both synthesis and internalization. It is thus quite conceivable that apoE depletion observed in the brain of apoE4 carriers may significantly compromise lipid delivery in the CNA. These results provide an intriguing new explanation for the reported reduction of cholesterol in the brain of AD subjects with unknown genotype.

EXAMPLE II

Correlations Between apoE4 Allele Copy Number and Senile Plaques and Neurofibrillary Tangles in Three Different Areas of the Hippocampus, Namely the CA 1 Sub-Field, Subiculum and the Parasubiculum in Individuals with Different apoE4 Allele Copy Number The results are summarized in FIG. 3 and below.

Methods

Genotype was determined as described for FIG. 1. Senile plaque and tangle density measures were performed as described before (Aubert, I. et al., 1992, J. Neurochem., 58:529–541). Paraffin embedded hippocampal tissue from 59 autopsied AD patients was obtained from the Douglas Hospital Brain Bank and stained with hematoxylin and eosin, modified Bielchowsky, and alkaline Congo red. Quantitative morphometric evaluations of neurofibrillary tangles and senile plaques were done as follows. A micrometric scale was used for calibration. Readings were done with a 10 X objective for plaques and 25X objective for tangles. Diffuse plaques were excluded from these measurements. Screening of alkaline Congo™ red stains under polarized light was used to control the reliability of tangle staining and, to a lesser extent, of senile plaque's affinity for the modified Bielchowsky preparation. Idiopathic Parkinson's disease (IPD) was diagnosed according to the presence of significant loss of pigmented neurons, Lewy bodies in residual neurons, clusters of macrophages, and gliosis in the pars compacta of the substantia nigra. These usually correlated with pre-mortem classical features of IPD, such as resting tremor, rigidity, and akinesia. Statistical analysis was performed using the Multivariate General Linear™ Models as part of the Systat Statistical Software™ package.

Results

The correlation between apoE4 allele copy number and the density of senile plaque is very strong in all three hippocampal regions. The correlation between apoE4 allele copy number and the neurofibrillary tangles index was also significant for the CA1 and the subiculum areas. These results support the concept that apoE4 plays a role in the pathophysiology of AD.

EXAMPLE III

Association Between Neurological Pathology and Acetylcholine Activity

Brain phospholipids such as PC and PE which have been shown to play an important role in the availability of choline, the rate-limiting precursor of acetylcholine (Ach). Brain levels of choline are decreased by 40–50% in AD frontal and parietal cortex (Nitch, R. M. et al., 1992, Proc. Natl. Acad. Sci., 89:1671–1675). Similarly, cholesterol is apparently required for the proper function of some cholinergic receptor sub-types (Jones, O. T. & McNamee, M. G., 1988, Biochemistry, 27:2364–2374). On the basis of possible interrelation ships between apoE4, senile plaque and neurofibrillary tangle counts and Ach, we evaluated the next possible association between the presence of apoE4 and cholinergic dysfunction, a classical hall mark of AD (Bowen, D. M. et al., 1981, N. Engl. J. Med., 305:1016; Whitehouse, P. J. et al., 1982, Science, 215:1237). We focused our attention on the determination of ChAT activity, the key enzyme involved in the synthesis of Ach, in post-mortem hippocampus and temporal cortex of individuals suffering from AD and in control subjects.

Methods

Figure 4A:
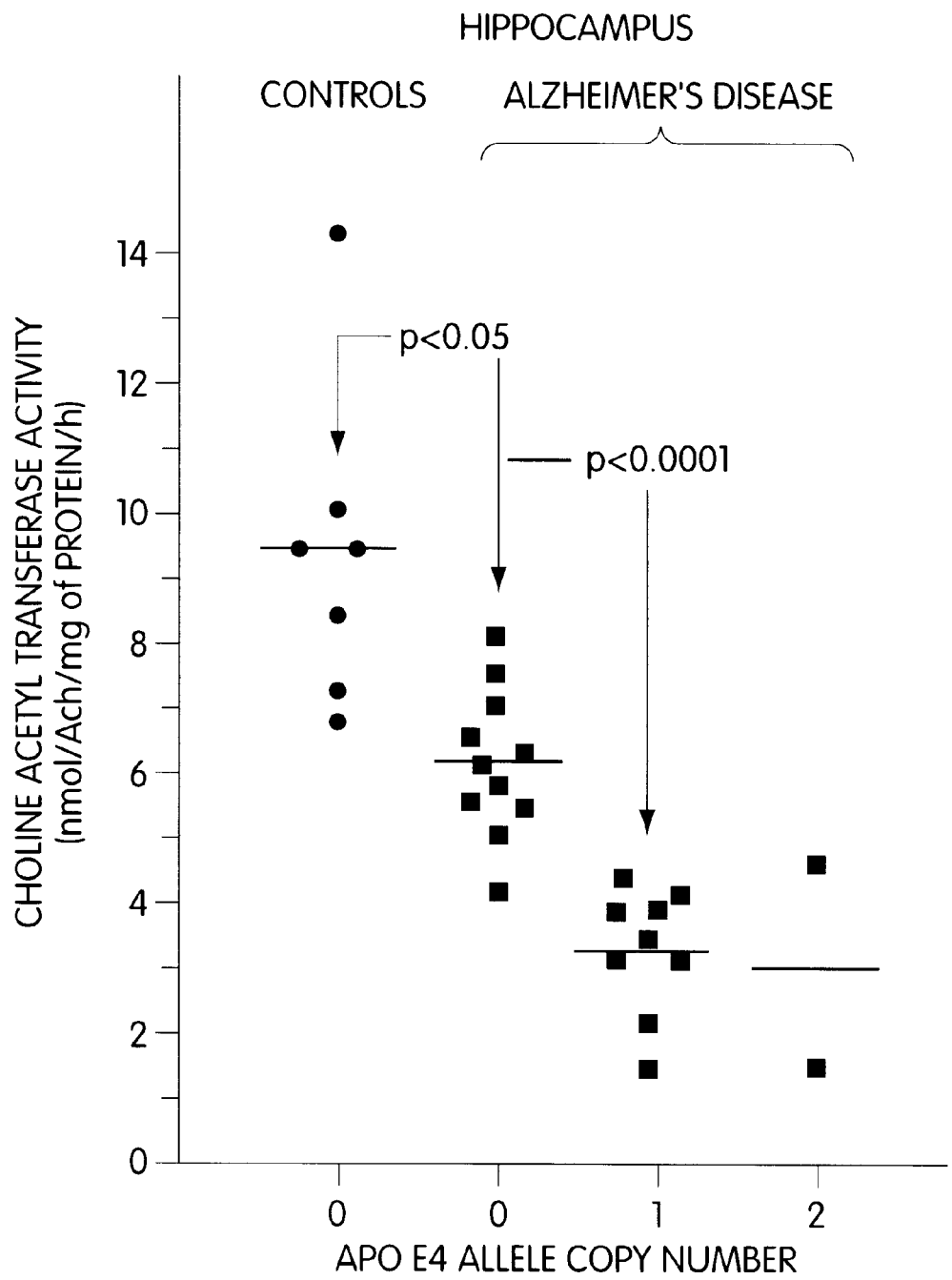
FIGS. 4A and 4B are graphs illustrating E4 allele copy number and choline acetyltransferase activity in Alzheimer's disease.
Figure 4B:
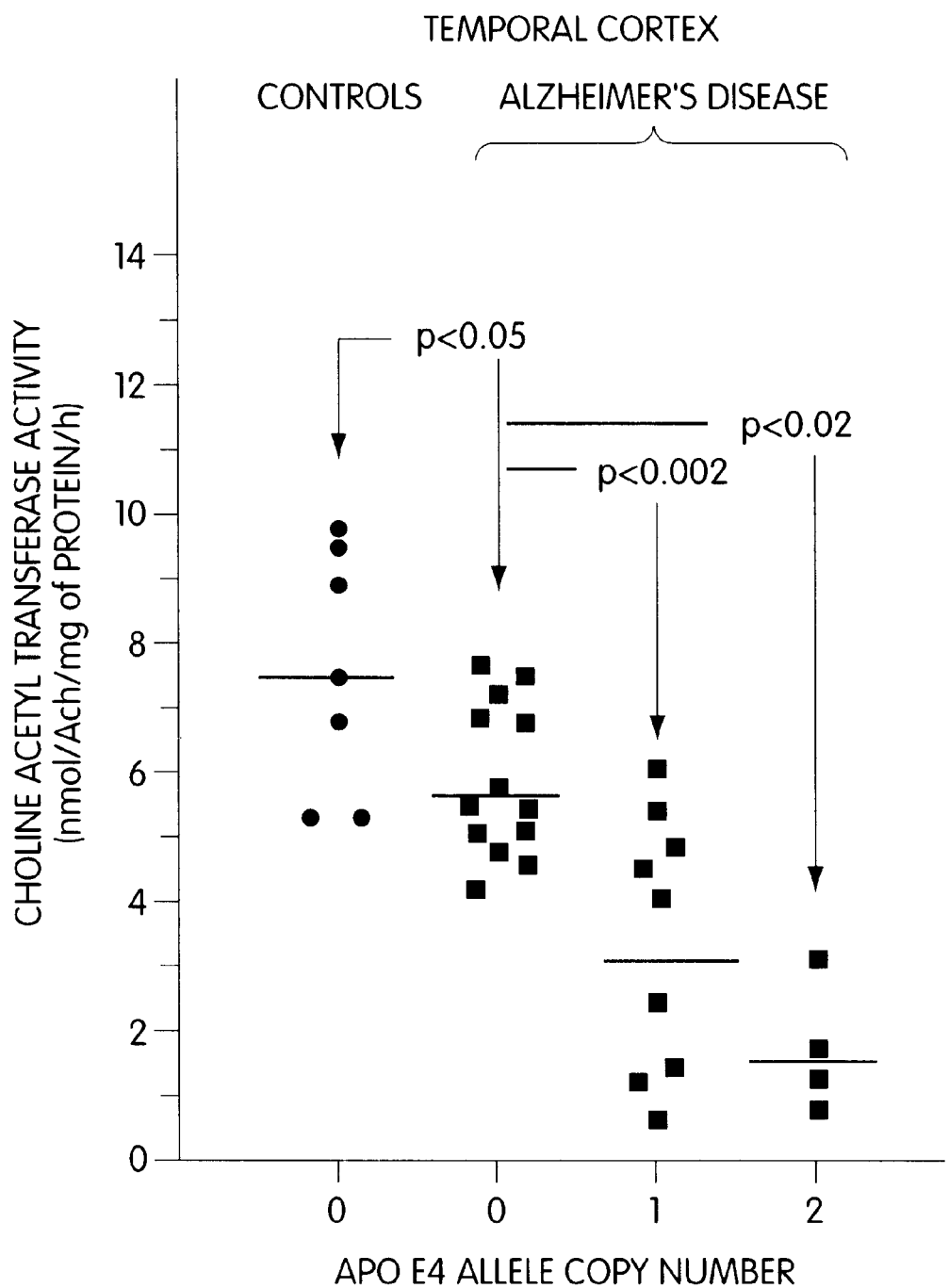

FIGS. 4 and 6 illustrate the effect of the presence of apoE4 isoform on hippocampal and temporal cortex ChAT activity.

Left hemisphere to be used for biochemical assays were sectioned in to thick (10 mm) coronal slices quickly and deeply frozen in 2-methylbutane at −40° C. before storage at −80° C. Tissues from hippocampal and temporal cortical areas were homogenized and incubated for 15 min. in buffer containing [14C] acetyl-CoA as previously described in detail elsewhere (Aubert, I. et al., 1992, J. Neurochem., 58:529–541). The post-mortem diagnostic was performed as described for FIG. 3. Apolipoprotein E genotype was determined as described for FIG. 1.

Results

Highly significant reductions in ChAT activity were seen in apoE4 carriers. In the hippocampus (22 ADs and 7 controls), ChAT activity values are 9.44±0.93 (control apo E3/3, no apoE4 allele), 6.09±0.36 (AD apoE3/3, no apoE4 allele), 3.21±0.31 (AD apoE4/3) and 2.94±1.52 (AD apoE4/4) nmol Ach/mg protein/hr, respectively. Statistical analyses indicate that control apoE3/3 ChAT values are significantly different from the AD apoE3/3 group (p<0.05) and the apoE4/3 group (p<0.0001) whereas, AD apoE3/3 ChAT levels are significantly different from the AD apoE4/3 group (p<0.0001) and likely the apoE4/4 group, although statistical evaluation could not be performed because of the limited number of apoE4 homozygotes available. Similar results were obtained in the temporal cortex (26 ADs and 7 controls) with ChAT activity values of 7.48±0.74 (control apoE3/3), 5.65±0.33 (AD apoE3/3), 2.91±0.66 (AD apoE4/3) and 1.56±0.47 (AD apoE4/4) nmol ACh/mg protein/hr, respectively. Statistical analyses indicate that control apoE3/3 ChAT values are significantly different from all AD groups (p<0.05 for apoE3/3 and p<0.001 apoE4/3) whereas AD apoE3/3 ChAT levels are significantly different from the AD apoE4/3 group (p<0.002) and the apoE4/4 group (p<0.02).

Figure 5A:
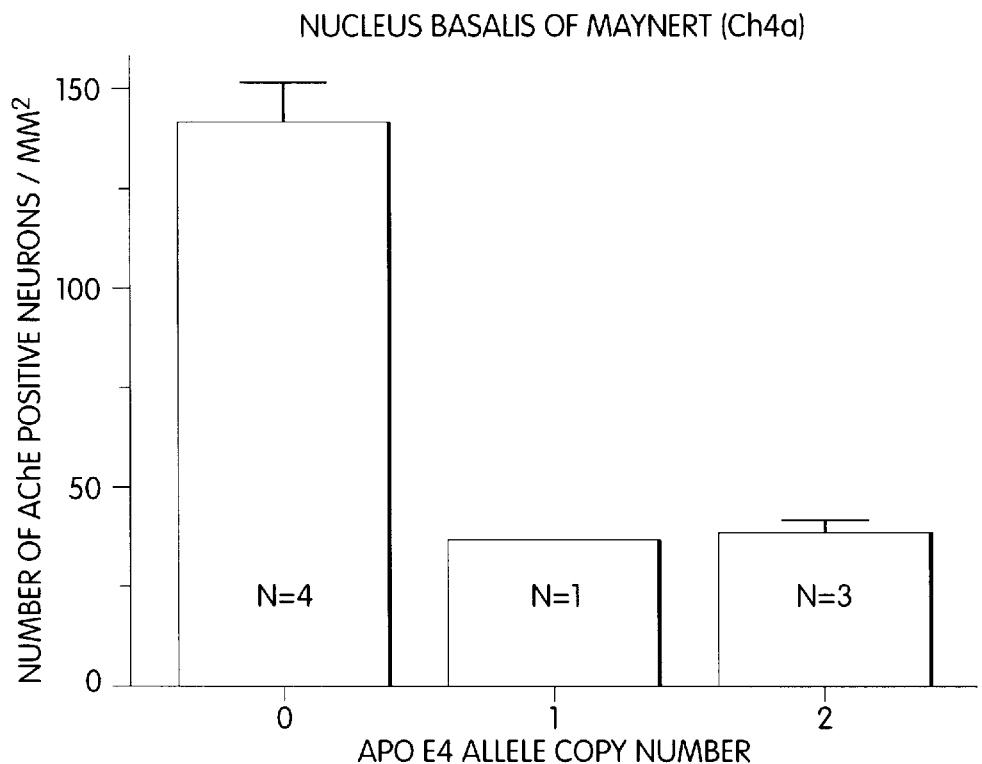
FIGS. 5A and 5B are graphs illustrating the loss of neurons which synthesize acetylcholine in the nucleus basalis of Meynert and in the diagonal band of Broca.
Figure 5B:
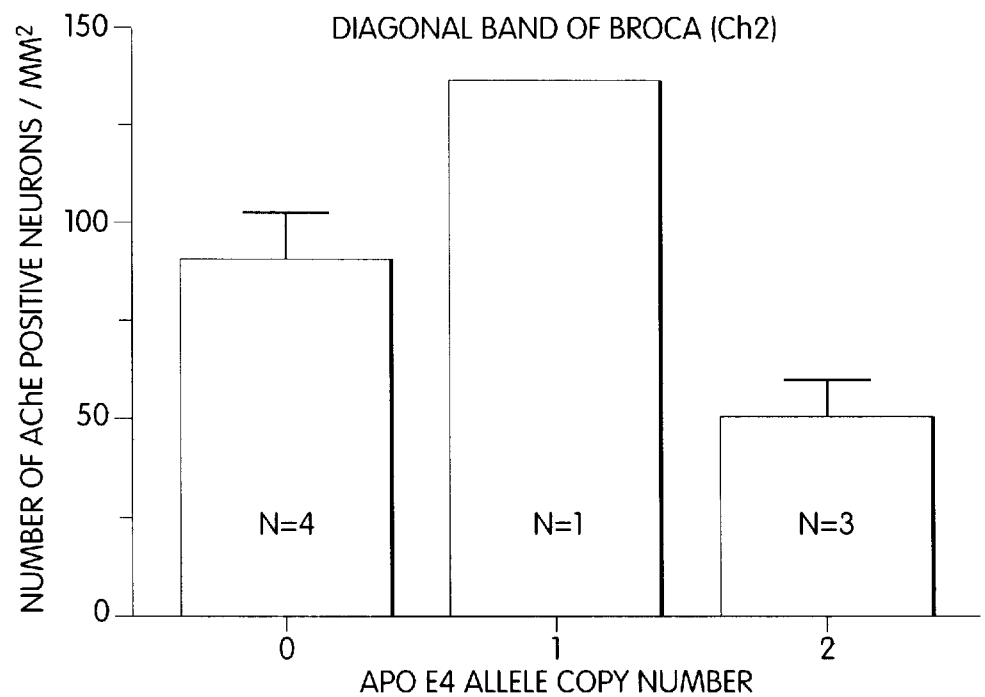
Figure 6A:
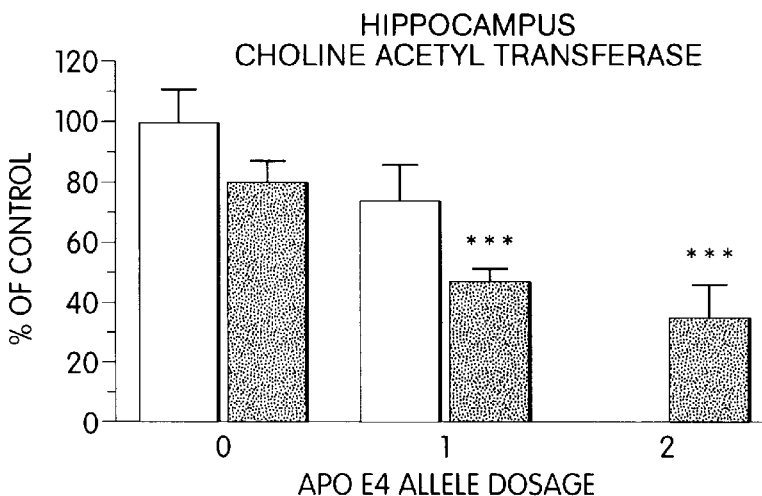
FIGS. 6A–6J are graphs illustrating the effect of apo E4 allele copy number on a) choline acetyltransferase activity, b) nicotinic receptor density, c) total muscarinic receptor density, d) muscarinic M1 (post-synaptic) and e) muscarinic M2 receptor density in post-mortem non-AD and AD brains in the hippocampal formation and temporal cortex.
Figure 6B:
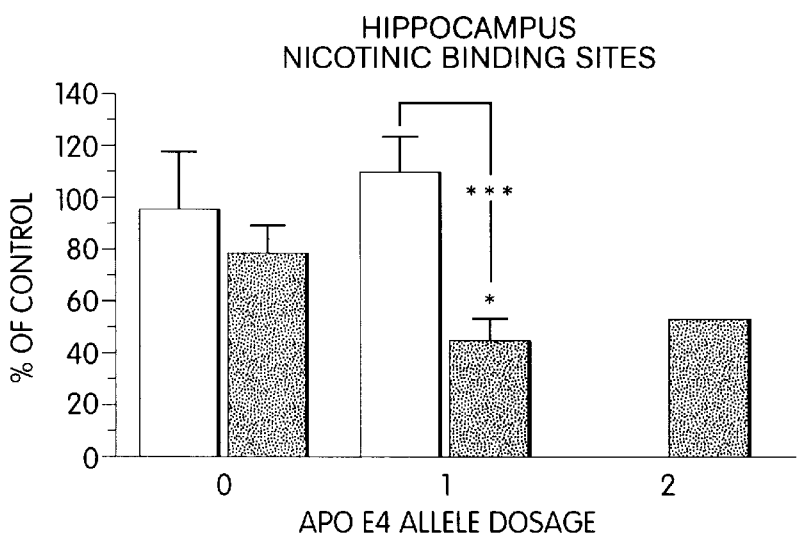
Figure 6C:
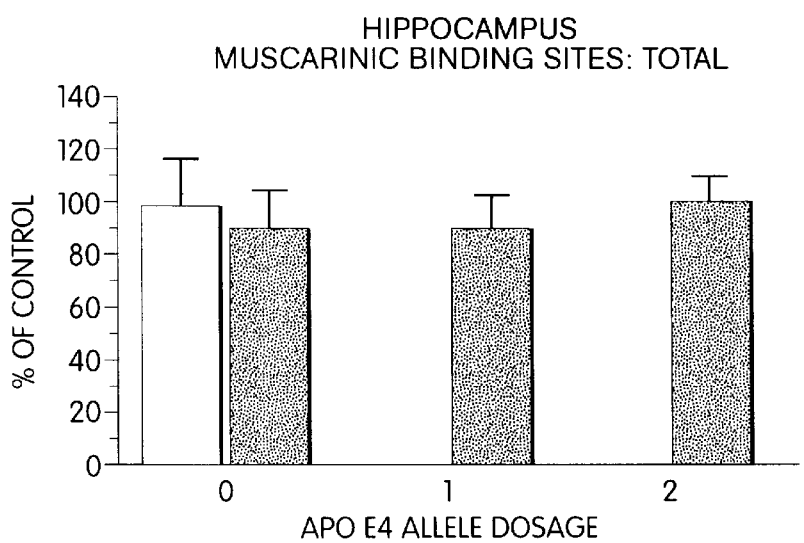
Figure 6D:
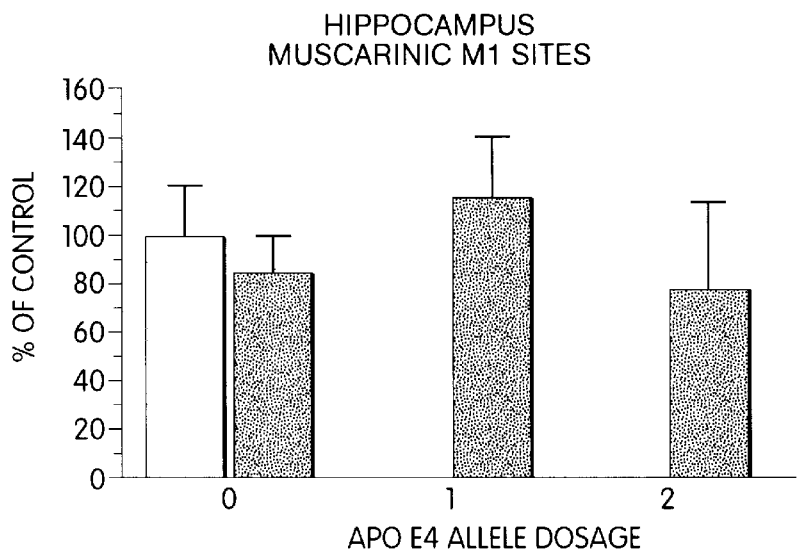
Figure 6E:
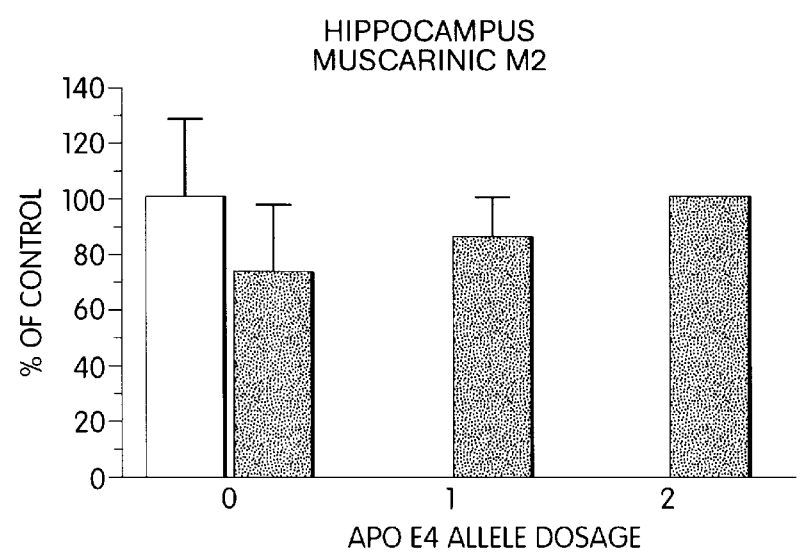
Figure 6F:
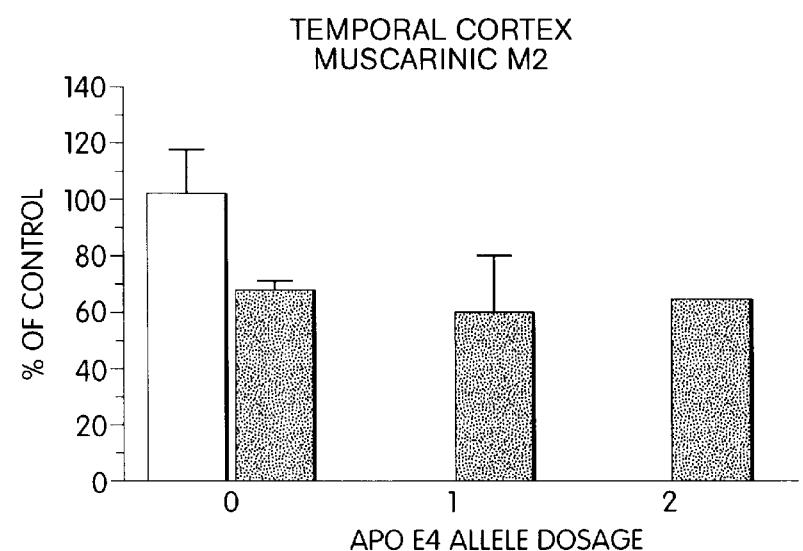
Figure 6G:
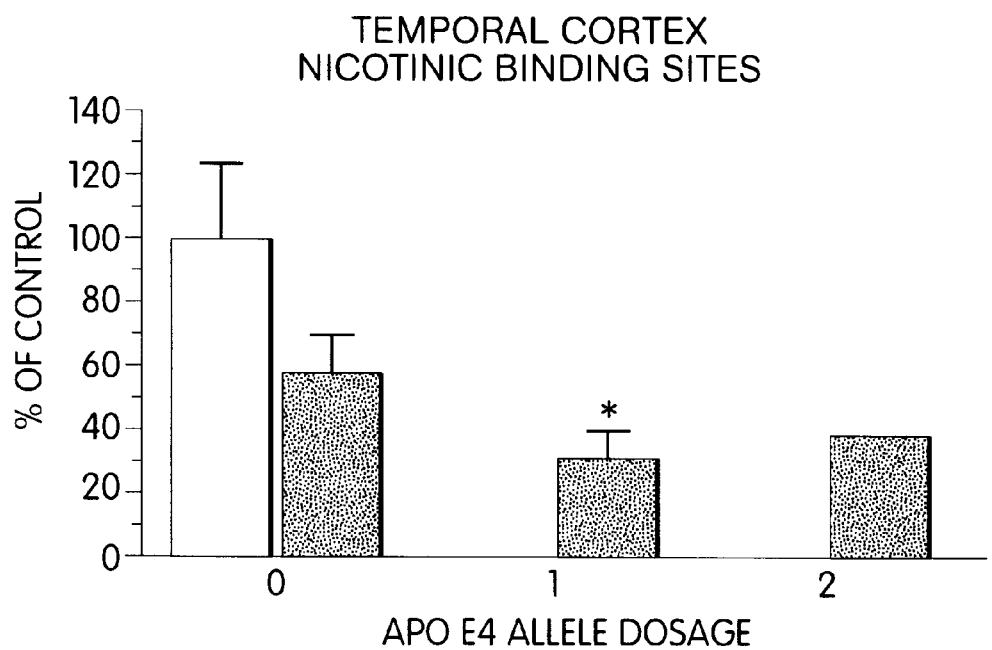
Figure 6H:
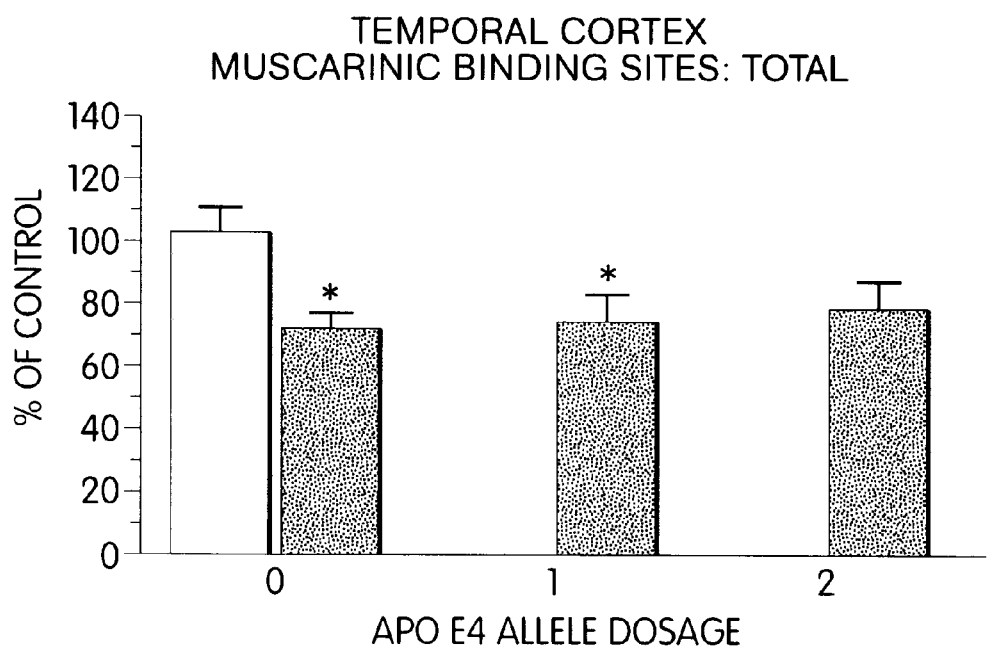
Figure 6I:
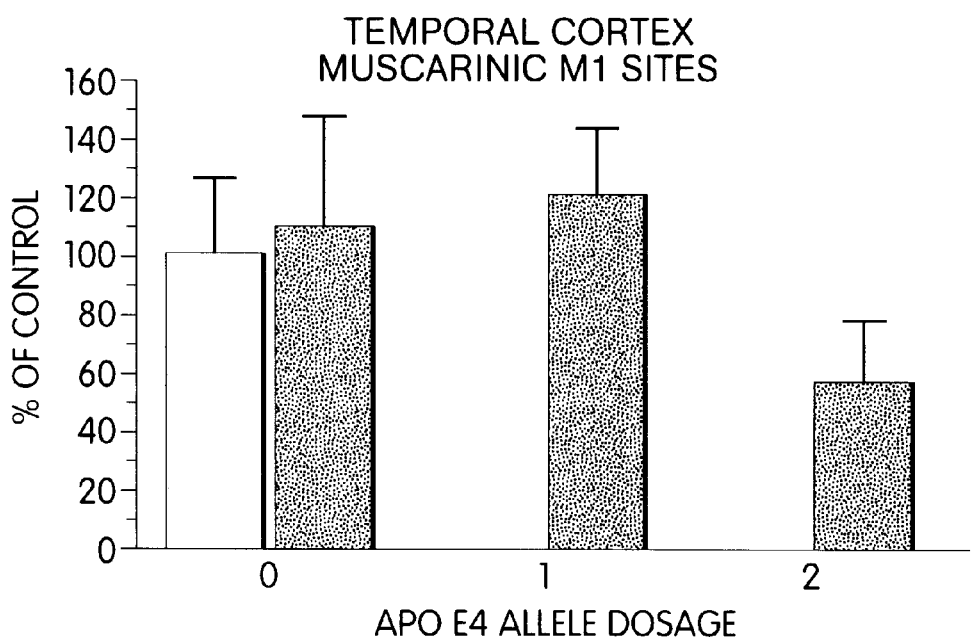
Figure 6J:
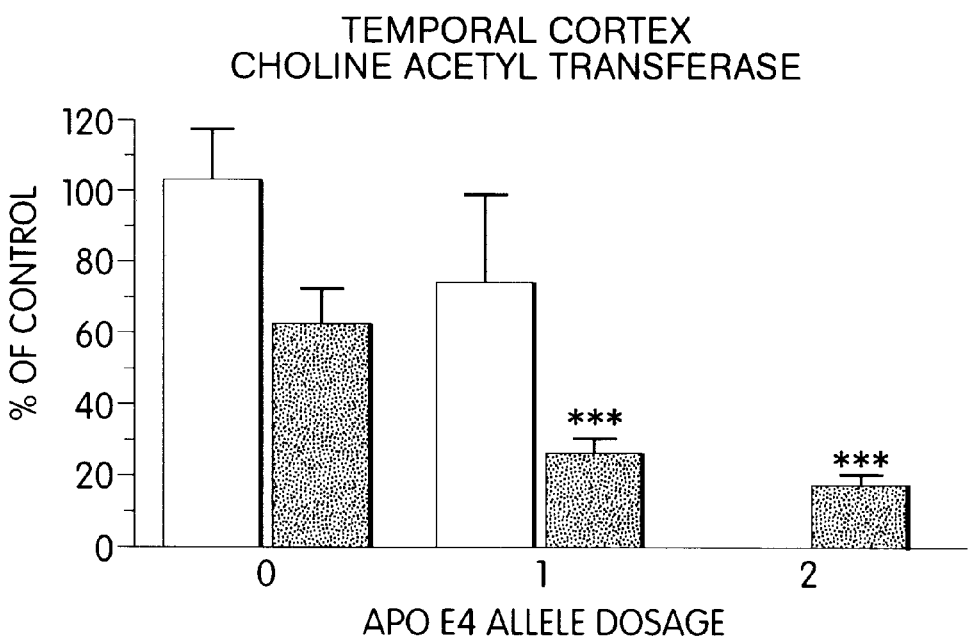

Without wishing to find ourselves bound to a particular explanation, the apoE4 allele copy number-rated reduction in ChAT activity and nicotinic receptors may be caused by at least one of two distinct phenomena. First, phospholipids such as PC and PE which can serve as precursors to choline in the synthesis of Ach could be transported into neurons via the classical apoE-LDL receptor pathway. An isoform-dependent impaired regulation of the transport of phospholipids in the brain of apoE4 carriers could explain the reduced levels of PC, PE and choline reported in AD; this then leading to decreased Ach synthetic capacities. Alternatively, the reduction in neuronal ChAT activities and choline levels could be secondary to losses of cholinergic neurons. Analysis of the number of acetyl cholinesterase-positive neurons in the nucleus basalis of Meynert (NBM) and diagonal band of Broca (DBB) of a small number of AD patients (n=7) revealed marked losses of cholinergic neurons in apoE4 versus apoE3 homozygous AD cases (↓70% in NBM and ↓45% in DBB, FIG. 5).

These results clearly indicate that there are distinct genetic entities in neurological disease and that these entities AD which show differential degrees of alterations of cholinergic activity, at least as revealed by ChAT activity and nicotinic receptors. Our data also suggest that cholinergic function in apoE3/3 bearers may be spared and that these patients could be better responders to a cholinomimetic-based therapy.

EXAMPLE IV

Additional Neurochemical Alterations and Therapeutic Response in Subjects Treated with Cholinomimetics Methods
i) Post-Mortem Study of Cholinergic Marker Case Selection and apoE genotyping: Frozen tissues from 84 autopsy confirmed cases of sporadic AD (35 females, 77.3+8.7 years: 49 males, 76.1+9.5 years) and from 14 control individuals (8 females, 71.6+3.6 years; 6 males, 66.4+3.1 years) were obtained from the Douglas Hospital Brain Bank in Montréal, Canada. The average post-mortem delay was 17.2+1.3 and 20.0+4.6 hours for AD and control subjects, respectively. It should be noted that the availability of apoE4/4 homozygous subjects is very limited, probably due to the fact that apoE4/4 homozygote individuals represent less than 1% of the entire population.

High molecular weight DNA for genotype analysis was isolated from frozen cerebellum or temporal cortex as adapted from (Nalbantoglu, J. et al., 1994, Predictive value of apolipoprotein E4 mutation in Alzheimer's Disease, Ann. Neurol. 36:889–895). ApoE genotype was determined by allele-specific extension of purified brain DNA using (Nalbantoglu, J. et al., 1994, Predictive value of apolipoprotein E4 mutation in Alzheimer's Disease, Ann. Neurol. 36:889–895). The primers labeled D, E, F, G, and H were synthesized for us by Genosys Biotech (The Woodland, TX); primer sequences are given in Main et al. (Main, R. F. et al., 1991, J. Lipid. Res., 32:183–187). Reactions were carried out in a volume of 50 uL containing 1 ug of DNA; deoxyadenosine triphosphate, deoxycytidine triphosphate, deoxythymidine triphosphate and deoxyguanosine triphosphate (Pharmacia Biotech, Montreal, CANADA.), each 0.2 mmol/L; 10% dimethyl sulfoxide; 12.5 pmol of either primer D, E, F, G; 25 pmol of primer H; and 10 uL of 10 PCR reaction buffer (Vector Biosystem, Toronto, CANADA). The DNA in the reaction mixture was first denatured for 10 min. at 96° C. and then cooled to 4° C. One unit of Taq polymerase (Vector Biosystem, Toronto, CANADA) was then added to each tube. Each sample was then reheated for 2 min. at 96° C. and subjected to 30 cycles in a thermal cycler with each cycle consisting of a 10 sec denaturation at 96° C., 30 sec annealing at 58° C. and 1 min. extension at 65° C. The reaction products were visualized by electrophoresis of 10 uL of the reaction mixture in a 1% agarose gel containing TPE buffer (0.08 mol/L Tris-phosphate, 0.002 mol/L EDTA, Sigma, St. Louis, USA) and ethidium bromide (0.15 ug/mL) for 1 hr at 67 v. The gels were then photo graphed and the banding profile was compared to known standards.

Neuropathological Analyses

Neurofibrillary tangle and senile plaque indices were determined as described in detail elsewhere (Aubert, I. et al., 1992, J. Neuro chem., 58:529–541; Etienne, P. et al., 1986, Neuro science, 19:1279–1291). Fifteen micron paraffin embedded hippocampal sections were stained with either hematoxylin and eosin, modified Bielchowsky stain, and alkaline Congo red to visualize neurofibrillary tangles and senile plaques. Quantitative morphometric evaluation of neurofibrillary tangles and senile plaques were determined: using a micrometric scale for calibration readings were done with a 10 X objective for senile plaques and a 25X objective for neurofibrillary tangles. Diffuse plaques were excluded from all measurements. Screening of alkaline Congo red stains under polarized light was used to control for the reliability of tangle staining and, to a lesser extent, of the senile plaques' affinity for the modified Bielchowsky preparation. These criteria are consistent with those used in the classification of Khachaturian (Aubert, I. et al., 1992, J. Neurochem., 58:529–541)

ii) Cholinergic Function in the Post-Mortem Brain of Control and AD Subjects

Materials: [3H]QNB (45.7 Ci/mmol), [3H]PZ (87.0 Ci/mmol), [3h]AF-DX 116 (49.3, 57.0, or 70.0 Ci/mmol), [3H]MCC (84.5 Ci/mmol), and [4C]acetyl-CoA (48.8 mCi/mmol) are purchased from New England Nuclear (Boston, MA, U.S.A.). Nicotine (free base), atropine sulfate, choline chloride, and eserine hemisulfate salts are bought from Sigma Chemical Co. (St. Louis, MO, U.S.A.). ACH chloride was supplied by Hoffmann-LaRoche (Basel, Switzerland). Unlabelled acetyl-CoA are purchased from Boehringer Mannheim (Mannheim, F.R.G.). Tetraphenylboron™ (sodium salt) and 3-heptanone are purchased from Aldrich Chemical Co. (Milwaukee, WI, U.S.A.). Ethyl acetate was bought from American Chemicals Co. (Montreal, Quebec, Canada). Bovine serum albumin (98% fatty acid free) and Ecolite scintillation cocktail are purchased from ICN Bio chemicals (Irvine, CA, U.S.A.). Triton™ X-100 (100%) scintillation grade was from Amersham (Arlington, IL, U.S.A.). All other chemicals were from Fisher Scientific (Montreal, Quebec, Canada).

Human brain tissues are obtained at autopsy from individuals clinically diagnosed as having AD, PD, or PD/AD and from neurological normal age-matched controls. Tissues are provided by the Brain Bank of the Douglas Hospital Research Center (Y. Robitaille, neuropathologist). Histopathological criteria have been described earlier. Hemispheres to be used for bio chemical assays are sectioned into thick (10 mm) coronal slices quickly and deeply frozen in 2-methylbutane at −40° C. before storage at −80°. Before biochemical assays, brain slices are slowly thawed on a cold plate, and the following structures are dissected as follows: frontal (Brodmann areas 9 and 10) and temporal (Brodmann areas 20, 21, 22, and 38) cortices, hippocampus and cerebellum (use as a low pathology brain area).

iii) Analysis of the Results

Binding parameters (Kd and Bmax values) were derived from the saturation experiments analyzed by the computerized method LIGAND™ (Aubert, I. et al., 1992, J. Neurochem., 58:529–541). Statistical significance of differences between control and AD (0, 1, 2 copies of E4 alleles) brain was evaluated using Student's unpaired t test, with values of $p<0.05$ being considered significant.

iv) Assay for Choline Acetyltransferase (ChAT) Activity

Tissues from various brain regions were homogenized and incubated for 15 min. in buffer containing [14C]acetyl-CoA as previously described in details (Aubert, I. et al., 1992, J. Neurochem., 58:529–541) to determine ChAT activity.

Multiple biochemical and anatomopathological studies have shown that the immunoreactivities and activities of cholinergic marker enzymes, such as ChAT, decrease in the neocortex as well as in the hip pocampus of patients with AD. As shown in FIG. 6, the apoE4 allele copy number is inversely correlated with ChAT activity in the hippocampus and temporal cortex of age-matched control and AD subjects. In FIGS. 6A–J each bar refers to mean value+S.E.M. Significant differences between groups are indicated by the number of stars: *: $p<0.05$, : $p<0.01$, *<0.001. Striking reductions in ChAT activity were seen in apoE4 carriers. ChAT values are represented in FIG. 1 in the hippocampus (23 ADs and 30 controls) and temporal cortex (30 ADs and 12 controls) of AD subjects with different doses of apoE4 allele.

Statistical analyses indicate that ChAT levels in AD subjects (with 1 and 2 copies of apoE4) are significantly different from AD from control subjects (with 0 or 1 copy of apoE4).

Figure 7:
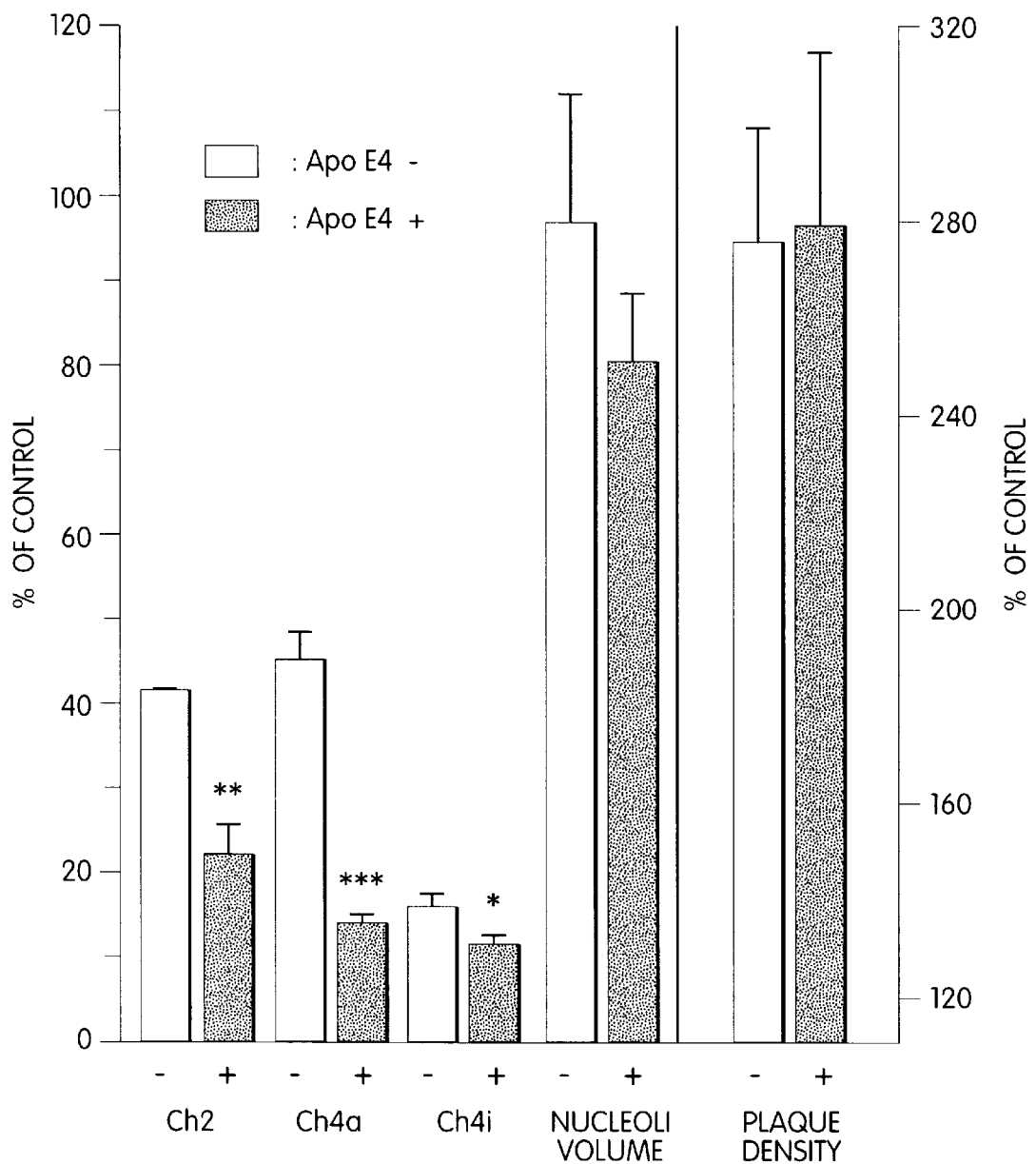
FIG. 7 is a graph illustrating the individual neuropathological and morphological characteristics associated to the cholinergic system in the brain of the various Alzheimer's disease and control cases investigated.

Acetylcholinesterase positive neuron density in the subcortical areas projecting to the temporal cortex and hippocampal structures are represented in FIG. 7. Neuronal cell density in the Ch2, Ch4a and Ch4i are expressed as percent of control values. Nucleolar volume is expressed in um2. Plaque density is expressed as number per mm3 in the hippocampus of the same patients. Portion of these results were published by Etienne and Colleagues (1986, Neuroscience, 19: 1279–1291). The genotype of the original patients was unknown and could not be done then. Since then, we reanalyzed the data in subjects for which genotype could be determined. Three AD subjects are apoE4 negative whereas four AD subjects are apoE4-positive. Results clearly confirm previous findings that AD subjects show marked loss of cholinergic neurons in Ch2, Ch4a and Ch4i but also highlight the fact that the pre sent of the apoE4 allele potentiate significantly the loss of neurons in the Ch2 and Ch2a ($P<0.01$) and in the Ch4i ($p<0.05$).

v) Binding of [3H]QNB to Total Populations of Muscarinic Sites

Punches of cortical and subcortical tissues from control subjects and AD brains are homogenized, centrifuged, and resuspended in Krebs buffer as previously described in detail for [3H]PZ assay. Final membrane pellets are suspended in buffer at a concentration approximating 3.0–5.0 mg of protein/ml. Aliquots of membrane-enriched homogenate (0.6–1.0 mg of protein) are incubated in Krebs buffer in the presence of a saturating concentration of [3H]QNB (10 nM) for 60 min. at room temperature (23° C.) in a total volume of 0.5 ml. All assays are performed in duplicate. Bound [3H]QNB is separated from free ligand by rapid filtration under reduced pressure through Schleicher & Schuell No. 32 glass filters, presoaked in 0.1% polyethylenimine solution, using a Brandel Cell Harvester apparatus (Brandel, Gaithersburg, MD, U.S.A.). Filters are then rapidly washed with ice-cold buffer, three times with 4.5 ml each, before being dried. The radioactivity of the filters is determined by liquid scintillation counting using a Beckman model LS7000 scintillation counter at 48% efficiency. Nonspecific binding, defined in the presence of 1 $\mu$M atropine sulfate, represents usually <15% of total binding.

vi) Binding of [3H]PZ to Human Brain Muscarinic M1 Sites

Brain tissues are processed as previously described earlier. Aliquots of final homogenates are incubated in Krebs buffer with various concentrations of [3H]PZ (0.1–20 nM) for 60 min. at room temperature (23° C.). Assays are terminated and radioactivity is determined as described above for [3H]QNB binding. Nonspecific binding, defined in the presence of total binding at ligand concentrations approximating Kd values.

vii) Binding of [3H]AF-DX 116 to Human Brain Muscarinic Putative M2 Sites

Brain tissues are processed as described above for [3H] QNB. Aliquots of final homogenates are incubated in Krebs buffer with various concentrations of [3H]AF-DX 116 (0.1–20 nM) for 60 min. at 4° C. Assays are terminated and radioactivity is determined as described above for [3H]QNB binding. Nonspecific binding, defined in the presence of 1 $\mu$M atropine sulfate, represents usually <40% of total binding at ligand concentrations approximating Kd values.

Muscarinic binding sites (total, M1 or M2) are not altered in the hippocampus of AD versus control subjects. The apoE genotype has no significant impact on the activity of these receptors. Muscarinic M1 and M2 receptor sites are not alters in AD versus control subjects in the temporal cortex whereas the so-called total (QNB) muscarinic binding sites are slightly reduced in AD versus control subjects (no genotype effect on this receptor group).

viii) Binding of [3H]MCC to Human Brain Nicotinic Sites

Brain tissues are processed as described above for [3H] QNB with the exception that samples were homogenized in 50 mM Tris-HCl buffer. Aliquots of final homogenates were incubated in 50 mM Tris-HCl buffer with various concentrations of [3H]MCC (0.1–20 nM) for 60 min. at 4° C. Assays are terminated and radioactivity is determined as described above for [3H]QNB binding. Nonspecific binding, defined in the presence of 10 $\mu$M nicotine, represents usually <50% of total binding at ligand concentrations approximating Kd values.

Results

Nicotinic Receptor Binding Sites are significantly reduced in apoE4 AD subjects where AD subjects not carrying apoE4 are not different from controls subjects. This is valid for both the hippocampal and the temporal areas in AD.

These results are consistent with the notion that apoE genotype may directly influence the synaptic plasticity of the cholinergic system in response to neuronal cell loss. In this model, apoE4 compromises lipid homeostasis and consequently impairs membrane remodeling. The fact the cholinergic system is the only neurotransmitter system of the brain that requires lipid (not amino acids) to synthesize its neurotransmitter (the acetylcholine) further highlights the selective vulnerability of this system in a situation of poor lipid delivery and/or availability.

EXAMPLE V

Acetylcholinesterase-Inhibitor Treatment in Humans with AD

Clinical Effect of apoE Genotype

Study Design

The study was a 30-week study in which patients were randomized to one of four treatment groups: placebo or escalating doses of the acetylcholine esterase inhibitor Tacrine™.

Methods

In the tacrine treated group, all patients began treatment at 40 mg/day. One group had tacrine increased to 80 mg/day, on which they remained until the end of the study. The other two groups received tacrine in dosages escalated beyond 80 mg/days to 120 and 160 mg/day. Only the latter group of patients considered in the present genotype analysis.

Forty AD patients who received the maximum dose of tacrine (40 mg/d for 6 weeks, 80 mg/d 6 weeks, 120 mg/d for 6 weeks 160 mg/d for 12 weeks for a total of 30 weeks) and completed the drug trial were selected to determine apoE phenotype using serum proteins described before (above and Poirier et al., 1993, Apolipoprotein E phenotype and Alzheimer's Disease, Lancet 342:697–699). The patients selection done on the basis of presence and absence of drug response to the treatment. The Alzheimer's Disease Assessment Scale (ADAS) used to monitor treatment effects. Half of the selected patients showed drug responsiveness (positive AD differences) or lack of response (negative AD data). I then examined the impact of different genotypes (apoE2/2, 3/2, 3/3, 3/4, 2/4 and 4/4) on therapeutic response using the ADAS-cog and the AD total test results obtained prior to and after tacrine administration. The ADAS-cog is an objective test that evaluates memory, attention, reasoning, orientation and praxis: a decrease score over time (or a positive difference) indicates improvement (Rosen, W. G. et al., 1984, Am. J. Psychiatr., 141:1356–1364). The AD total includes the cognitive and non-cognitive portion of the ADAS.

Results

Cholinergic Drug Response in Genotyped AD Subjects

Figure 8B:
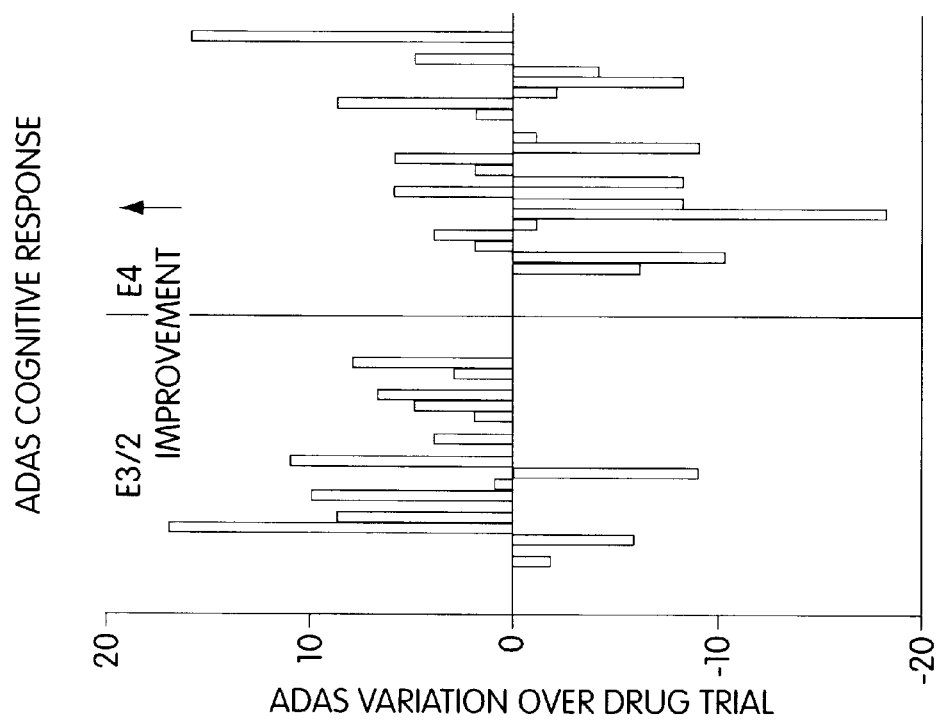
FIGS. 8a and 8b are graphs illustrating the AD assessment scale (ADAS) delta values (end values minus screen values) in tacrine-treated AD patients with different apoE genotype.
Figure 8A:
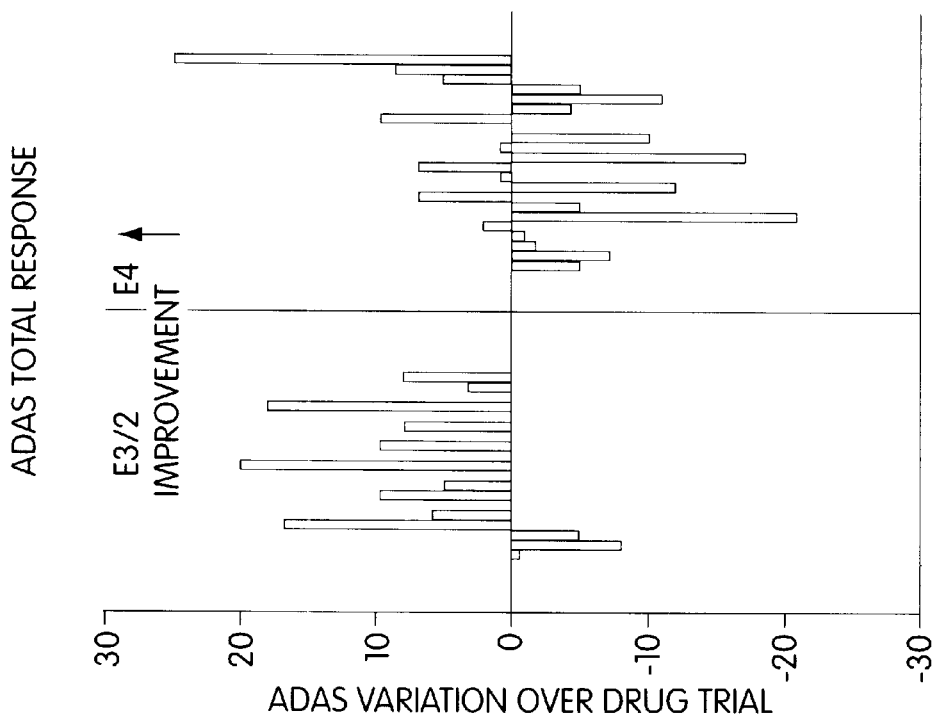
Figure 9A:
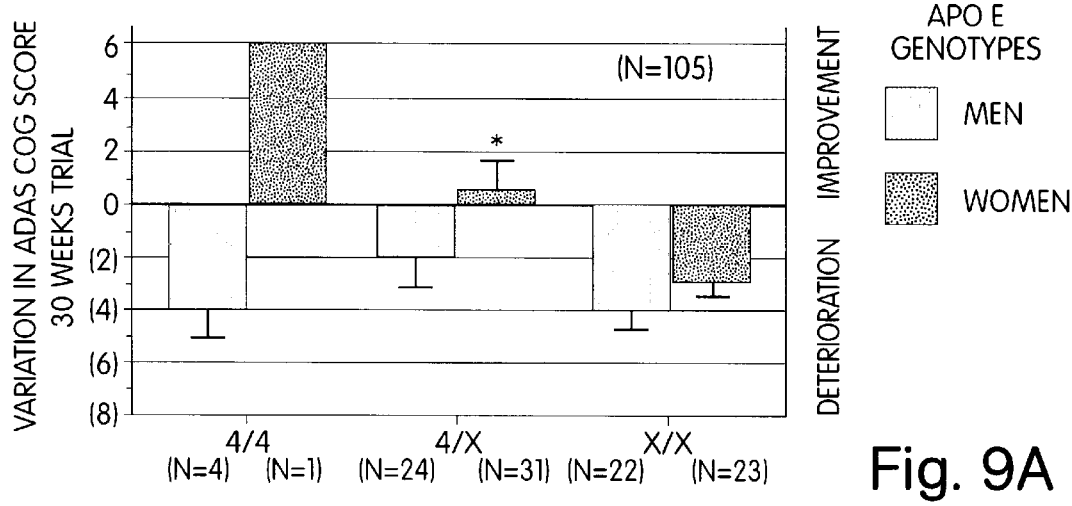
FIGS. 9A and 9B are graphs of the ADAS-COG Scores with tacrine and tanoneline, respectively, from day 0–week 30.
Figure 9B:
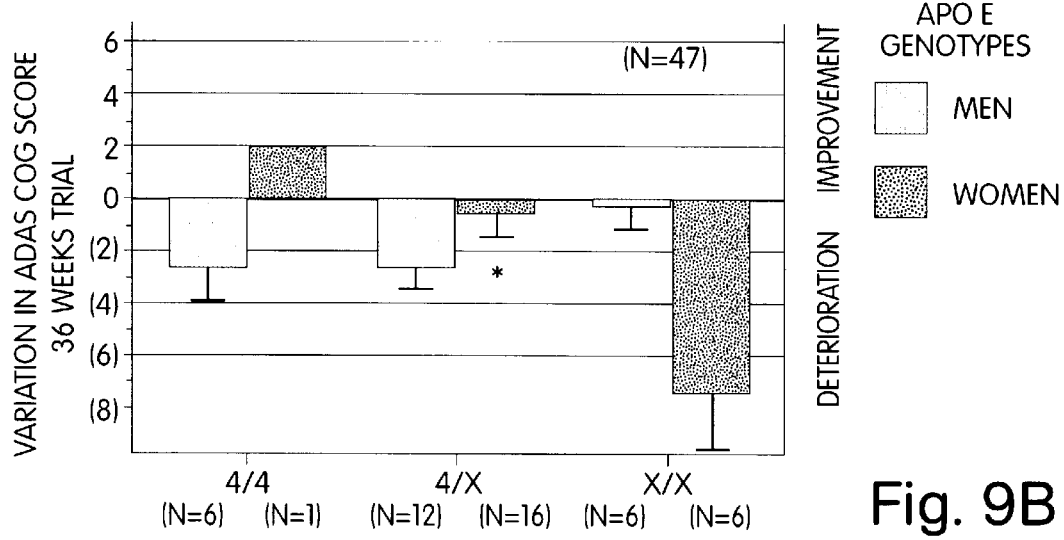

FIG. 8 illustrates the drug responsiveness (ADAD-cog and AD total) of AD subjects a function of apoE4 allele. Each bar represents an individual subjects. Positive delta values (difference in AD score at the end minus AD score prior to drug treatment) indicate improvement in cognitive performance (ADcog) and in global performances (ADAS-total). Negative values represent patients who deteriorated over time and drug treatment. All the subjects are AD subjects, all were treated with the same drug, at the same level, for the same duration. The only critical factor that differentiates them is the presence or absence of the apoE4 allele.

Result clearly indicates that more than 85% of the apoE4 negative subjects show improvement with tacrine administration (AD total) where 60% of the apoE4 positive subjects are worse following drug treatment. In other words, 4 out 5 subjects that do not respond to tacrine are apoE4 positive.

The ADAS-cog scale shows similar response profile in apoE4 carriers and non-carriers.

Taken together, the data clearly suggest that cholinergic function in AD-E3/3, 3/2 and 2/2 subjects are at least partially spared when compared to AD-E4/3, AD-E4/2 and AD-E4/4 carriers. Most importantly, this genetic susceptibility apparently results in sub-groups of AD patients which respond differently to cholinomimetic-based therapies; with E4 carriers at a greater risk for loss of their Ach synthetic capacities. This hypothesis formally tested in tacrine-treated AD subjects which showed different apoE genotypes. As expected, apoE4 negative subjects were found to respond tremendously well to the acetyl cholinesterase inhibitor tacrine (an acetylcholine metabolism enhancer) when compared to apoE4 carriers.

The cholinergic hypothesis of geriatric memory dysfunction (Bartus, R. T. et al., 1982, Science, 217:408–417) raises some fundamental questions regarding the observed heterogeneity of clinical responses toward various cholinomimetics in different AD patients. The absence of clear beneficial effects of choline and lecithin in geriatric patients with and without AD have always been quite perplexing. Furthermore, clinical trials based on the use of esterase inhibitors such physostigmine tacrine (Davis, K. L. et al., 1992, N. Engl. J. Med. 327:1253–1259) have shown that contrary to young subjects, the optimal acute dose necessary to facilitate performance on memory tasks varied considerably among individual aged control subjects and AD patients.

The presence of the apoE4 allele appears now to be the most important factor responsible for individual variations in residual brain cholinergic innervation in AD and clearly predict clinical outcome of cholinergic based therapies. Clinical responsiveness to cholinergic agents monitored in genotyped AD patients demonstrated that apoE4 carriers are unlikely to be good responders, at least with the use of Ach precursors and esterase-based therapies.

EXAMPLE VI

Effects of Sex and apoE Genotype on Drug and Drug Dosage Efficiency

In this example we characterize patients with AD recruited for a large multi center study of tacrine and to investigate the impact of apoE allele load on short-term outcomes in placebo-treated patients, short-term tacrine treatment effects, and long-term treatment outcome. The patients were classified by sex and dosage. The results are summarized in Table I.

Method
i) Study Design

The 30-week study was randomized, double-blind, placebo-controlled, parallel-group clinical trial conducted at 33 centers in the USA (see Knapp, M. J. et al. JAMA 271: 985–991 (1995) for complete methodology). Patients randomized to tacrine treatment received an initial dose of 40 mg/day (10 mg QID) and were force-titrated at 6-week intervals in increments of 40 mg to maximum dose levels of 80, 120, and 160 mg/day for Groups II, III, and IV, respectively. Group I received placebo for the entire 30 weeks. The protocol was approved by Institutional Review Boards for each study center and followed guidelines of the Declaration of Helsinki and Good Clinical Practices.

Patients who completed the 30-week study well patients who terminated early were eligible to receive long-term, open-label, tacrine treatment. In the open-label phase, the initial dose for all patients with 40 mg/day (10 mg QID) which could be increased every 4 weeks in 40-mg increments to a maximum dose of 160 mg/day. The protocol specified visits in the open-label phase occurred every 3 months once a patient reached a stable dose. Dosage records were available for all patients. Approximately 2 years after the last patient completed the double-blind phase, the protocol was amended to allow genotyping of baseline plasma samples and collection information about nursing home placement (NHP) and mortality. Attempts were made, through the study centers, to contact the families of all 663 patients who were originally randomized.

ii) Patient Population

Patients eligible for the 30-week study were men and women, at least 50 years of age, meeting National Institute of Neurological and Communicative Disorders and Stroke (NINCDS) criteria for a diagnosis of probable AD. Patients were otherwise healthy and did not have significant extra pyramidal, cerebrovascular, cardiac, or hepatic disease; insulin-dependent diabetes mellitus; or chronic renal insufficiency. Disease severity at the time of study entry was defined mild to moderate based on Mini-Mental State Examination. (MMSE) scores between 10 and 26 inclusive. Written informed consent was obtained from care givers and patients or their legal representatives. Medications with known central nervous system effects were prohibited during double-blind treatment. Once patients completed or terminated from the double-blind phase of the study there were no restrictions on concurrent medications. Patients who stopped Tacrine™ treatment could take other investigational drugs.

iii) Outcome Measure

The ADAS-Cog is an objective test that evaluates memory, language, and praxis and is a sensitive measure of patient performance (maximum severity score of 7). A decrease in score indicates improvement.

The CIBIC is a global evaluation of change and is intended to determine whether the effects of an antidementia drug are large enough for detection by an experienced, skilled clinical observer during a comprehensive clinical interview with the patient. At baseline, input from the patient and family members are accepted in addition to a review of the patient's test performance. During subsequent visits, the clinician's assessment is based solely on an interview with the patient, without regard to test performance or family observations. The patient is rated on a 7-point scale: 1, very much better; 4, no change; and 7, very much worse.

The FCCA is also a 7-point scale. Similar to the CIBIC, a review of psychometric test scores is excluded, but input from family members is allowed. The FCCA was conducted after the CIBIC and only when the patient completed or withdrew from the study.

Each site provided data on the dates of death and/or NHP if either occurred during the 2-year follow-up period.

iv) Statistical Methods

Four comparisons of tacrine 160 mg/day versus placebo were conducted: (1) without adjusting for ApoE4; (2) adjusting for the presence or absence of ApoE4; (3) for patients with Apo E4; and (4) without Apo E4. The estimated treatment differences, 95% confidence intervals for the treatment differences, and parametric p-values were computed from an analysis of variance (ANOVA) that included effects for randomized treatment group (placebo, 80 mg/day, 120 mg/day, and 160 mg/day) and study site. An analysis of covariance (ANCOVA) for ADAS-Cog also included baseline score a covariant. Least-square means were used to estimate the effect of the E4 allele on Week 30 efficacy scores.

Similar ANOVA and ANCOVA models that included effects of treatment group, ApoE4 genotype, site and baseline score (for ADAS-Cog), and treatment×Apo E4 interactions were used to test the generalizability of the main effects of treatment in populations with and without the E4 allele.

CIBIC and FCCA scores were analyzed using Cochran-Mantel-Haenszel (CMH) methods on modified ridit scores, stratifying by site in the unadjusted analyses and stratifying by site and Apo E4 status in the adjusted analyses. Non-parametric p-values for CIBIC and FCCA were used to determine if tacrine treatment effects were statistically significant.

The change in ADAS-Cog scores at Week 30 were estimated for: (1) placebo patients with an E4 allele, (2) placebo patients without an E4 allele, (3) tacrine 160 mg/day patients with an E4 allele, and (4) tacrine 160 mg/day patients without an E4 allele using ANCOVA that adjusted for site and baseline score. Similarly, Week 30 CIBIC and FCCA scores were estimated using ANOVA adjusted for study site effects.

PROC LOGISTIC[21] adjusted for baseline Instrumental Activities of Daily Living (IADL), other investigational anti-dementia agents, age, gender and presence or absence of the E4 allele was used for performing logistic regressions[22] to analyze NHP and mortality data. Patients were grouped according to the last daily dose of tacrine received (0–40 mg/day, >40–80 mg/day, >80–120 mg/day, and >120–160 mg/day). Estimated treatment differences between the 0 to 40 mg/day group and other 3 groups were computed using odds ratios. To check for generalizability of the effect of the last daily dose of tacrine, a similar model included additional indicator variables for treatment×Apo E4 interactions. NHP and mortality data were also analyzed without adjusting for the presence or absence of the E4 allele for all randomized patients and for patients with and without the E4 allele.

Results

Table I shows, correlation of the drug dosage, patient sex, and apoE allele load a critical element of the appropriate treatment protocol. For example, men having no E4 allele do best with either low or high doses, men with a single E4 allele require a high dose for maximum effect, and men having two E4 alleles do not respond to tacrine. By contrast, women having no E4 allele do best with a mid-level tacrine dose, while those with one E4 allele do equally well at any dose. Like men, those women having two E4 alleles do not respond to tacrine. When the above are incorporated into the pharmacogenetic approach, our method allows one to provide the clinician and the patient with a report having the lowest dose which indicates the highest effectivity for a given patient. This finding allows for correlation of the maximum level of therapeutic drug responsiveness with the minimum level of side effects.

TABLE 1

| BEST RESPONDERS AND Apo E ADAS-COG IMPROVE | | | |
|---|---|---|---|
| | E4/4 | E4/X | EX/X |
| MEN | | | |
| PLACEBO | 0 | 24 | 14 |
| Tacrine low | 0 | 14 | 33 |
| Tacrine mid | 0 | 34 | 0 |
| Tacrine high | — | 69 | 29 |

TABLE 1-continued

| BEST RESPONDERS AND Apo E ADAS-COG IMPROVE | | | |
|---|---|---|---|
| | E4/4 | E4/X | EX/X |
| WOMEN | | | |
| PLACEBO | 0 | 26 | 14 |
| Tacrine low | 0 | 20 | — |
| Tacrine mid | 0 | 24 | 67 |
| Tacrine high | — | 20 | 43 |

% of subjects with an improvement of the ADAS-COG score by at least 5 points on the scale

OTHER EMBODIMENTS

While the invention been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

I claim:

1. A method for determining the prognosis and ability of a patient diagnosed with a non-Alzheimer's disease (non-AD) neurological disease to respond to therapy comprising the following:
    a) identifying a patient who has been diagnosed with a non-AD neurological disorder;
    b) determining the apolipoprotein E (apoE) allele load of said patient through genotypic or phenotypic methods, said phenotypic methods including determining the apoE protein isoform; and
    c) utilizing the data obtained from step b) in a prognostic protocol; wherein the presence of at least one apoE ε4 allele in said patient is indicative of said patient having a poor prognosis of recovery and a decreased responsiveness to therapy.

2. The method of claim 1, wherein said method further comprises obtaining a patient profile.

3. The method of claim 1, wherein said patient is diagnosed with a disease selected from the group consisting of prion diseases, a pathology of the developing nervous system, a pathology of the aging nervous system, nervous system injury, coma, infection of the nervous system, a dietary deficiency, and a cardiovascular injury.

4. The method of claim 3, wherein said prion disease is Creutzfeldt-Jakob disease.

5. The method of claim 3, wherein said patient has been diagnosed with a congenital defect in amino acid metabolism.

6. The method of claim 5, wherein said defect is selected from the group consisting of arginosuccinic aciduria, cystathionuria, histidinaemia, homocystinuria, hyperammonaemia, phenylketonuria, and tyrosinanaemia.

7. The method of claim 3, wherein said patient has been diagnosed with fragile X syndrome.

8. The method of claim 3, wherein said patient has been diagnosed with a disease selected from the group consisting of neurofibromatosis, Huntington's disease, depression, amyotrophic lateral sclerosis, multiple sclerosis, stroke, Parkinson's disease, and multiple infarcts dementia.

9. The method of claim 2, wherein said patient profile includes a determination of said patient's sex.

10. The method of claim 2, wherein said patient profile includes the patient's genotype.

11. The method of claim 10, wherein said patient's genotype is the presenilin genotype.

12. The method of claim 10, wherein said patient's genotype is the apolipoprotein C1 (apoC1) genotype.

13. A method of characterizing the genotype of a patient diagnosed with a non-Alzheimer's disease (non-AD) neurological disease who is in a clinical trial for the treatment of a non-AD neurological disease comprising the following:

a) determining the apolipoprotein E (apoE) allele load of a patient who has been diagnosed with a non-AD neurological disorder through genotypic or phenotypic methods, said phenotypic methods including determining the apoE protein isoform; and b) utilizing the data obtained from step a) in a prognostic protocol.

14. A method for determining the ability of a patient with a non-Alzheimer's disease (non-AD) neurological disease to respond to cholinomimetic therapy comprising the following:

a) determining the patient profile of said patient;

b) determining the apolipoprotein E (apoE) allele load of said patient through genotypic or phenotypic methods, said phenotypic methods including determining the apoE protein isoform; and c) utilizing the data obtained from step b) to assess the patient's responsiveness to cholinomimetic therapy;

wherein a patient lacking both apoE $\epsilon$4 alleles is expected to benefit from cholinomimetic therapies.

* * * * *